US011160876B2

(12) United States Patent
Markovic et al.

(10) Patent No.: US 11,160,876 B2
(45) Date of Patent: *Nov. 2, 2021

(54) METHODS AND COMPOSITIONS FOR TARGETING T-CELL CANCERS

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 110 days.

This patent is subject to a terminal disclaimer.

(21) Appl. No.: 16/330,028

(22) PCT Filed: Aug. 31, 2017

(86) PCT No.: PCT/US2017/049745
§ 371 (c)(1),
(2) Date: Mar. 1, 2019

(87) PCT Pub. No.: WO2018/045238
PCT Pub. Date: Mar. 8, 2018

(65) Prior Publication Data
US 2019/0201546 A1 Jul. 4, 2019

Related U.S. Application Data

(60) Provisional application No. 62/382,635, filed on Sep. 1, 2016.

(51) Int. Cl.
| | | |
|---|---|---|
| *A61K 39/395* | (2006.01) | |
| *A61K 47/69* | (2017.01) | |
| *A61K 9/51* | (2006.01) | |
| *A61K 31/337* | (2006.01) | |
| *A61K 47/68* | (2017.01) | |
| *C07K 16/28* | (2006.01) | |
| *A61P 35/00* | (2006.01) | |
| *A61K 9/00* | (2006.01) | |
| *A61K 39/00* | (2006.01) | |

(52) U.S. Cl.
CPC ........ *A61K 47/6929* (2017.08); *A61K 9/0019* (2013.01); *A61K 9/5169* (2013.01); *A61K 31/337* (2013.01); *A61K 39/39558* (2013.01); *A61K 47/6849* (2017.08); *A61K 47/6867* (2017.08); *A61P 35/00* (2018.01); *C07K 16/2809* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic et al. |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |

(Continued)

FOREIGN PATENT DOCUMENTS

| | | |
|---|---|---|
| EP | 1913947 | 4/2008 |
| EP | 3204413 | 8/2017 |

(Continued)

OTHER PUBLICATIONS

U.S. Appl. No. 15/225,542; office action dated Jul. 18, 2019.
U.S. Appl. No. 15/452,069:office action dated Jun. 24, 2019.
U.S. Appl. No. 15/456,377; office action dated Jul. 5, 2019.
U.S. Appl. No. 15/456,382; office action dated Jul. 8, 2019.
U.S. Appl. No. 15/456,391 office action dated Jul. 24, 2019.
Beers et al. "CD20 as a Target for Therapeutic Type 1 and II Monoclonal Antibodies", Seminars in Hematology 47(2):107-114,(2010).
Belldegrun et al. "Human Renal Carcinoma Line Transfected with Interleukin-2 and/or Interferon alpha Gene(s); Implications for Live Cancer Vaccines", J National Cancer Institute 85(3):207-216 (1993).

(Continued)

*Primary Examiner* — Yunsoo Kim
(74) *Attorney, Agent, or Firm* — Baker Botts L.L.P.

(57) ABSTRACT

Described herein are compositions of binding agents and carrier proteins, and at least one therapeutic agent, wherein the binding agents are capable of binding an antigen expressed on T-cells and methods of making and using the same, in particular, as a T-cell cancer therapeutic. Also described are lyophilized compositions of binding agents and carrier proteins, and at least one therapeutic agent, and methods of making and using the same, in particular, as a T-cell cancer therapeutic.

19 Claims, 1 Drawing Sheet

(56) References Cited

U.S. PATENT DOCUMENTS

| | | |
|---|---|---|
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Swiss et al. |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,833 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Neil et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |
| 2018/0235886 A1 | 8/2018 | Markovic et al. |
| 2019/0022188 A1 | 1/2019 | Markovic |
| 2019/0038761 A1 | 2/2019 | Markovic et al. |
| 2019/0099498 A1 | 4/2019 | Markovic et al. |
| 2019/0184032 A1 | 6/2019 | Markovic et al. |
| 2019/0202916 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |

FOREIGN PATENT DOCUMENTS

| | | |
|---|---|---|
| EP | 3533870 | 9/2019 |
| JP | S60146833 | 8/1985 |
| JP | S6178731 | 4/1986 |
| JP | H04504253 | 7/1992 |
| JP | 2001072589 | 3/2001 |
| JP | 2012522809 | 9/2012 |
| KR | 1020090078330 | 7/2009 |
| RU | 2011133819 | 2/2013 |
| WO | 89/10398 | 11/1989 |
| WO | 97/49390 | 12/1997 |
| WO | 99/00113 | 1/1999 |
| WO | 99/51248 | 10/1999 |
| WO | 2004/022097 | 3/2004 |
| WO | 2004/096224 | 11/2004 |
| WO | 2006/034455 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | 2008/057562 | 5/2008 |
| WO | 2008/112987 | 9/2008 |
| WO | 2009/043159 | 4/2009 |
| WO | 2009/055343 | 4/2009 |
| WO | 2010/003057 | 1/2010 |
| WO | 2010/017216 | 2/2010 |
| WO | 2010/118365 | 10/2010 |
| WO | 2010/124009 | 10/2010 |
| WO | 2010/136492 | 12/2010 |
| WO | 2012/048223 | 4/2012 |
| WO | 2012/088388 | 6/2012 |

(56) References Cited

FOREIGN PATENT DOCUMENTS

| WO | 2012/154681 | 11/2012 |
|---|---|---|
| WO | 2014/009774 | 1/2014 |
| WO | 2014/037422 | 3/2014 |
| WO | 2014/055415 | 4/2014 |
| WO | 2014/105644 | 7/2014 |
| WO | 2014/123612 | 8/2014 |
| WO | 2015/048520 | 4/2015 |
| WO | 2015/191969 | 12/2015 |
| WO | 2015/195476 | 12/2015 |
| WO | 2016/057554 | 4/2016 |
| WO | 2016/059220 | 4/2016 |
| WO | 2016/089873 | 6/2016 |
| WO | 2017/031368 | 2/2017 |
| WO | 2017/062063 | 7/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 9/2017 |
| WO | 2018/027205 | 2/2018 |
| WO | 2018/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

Buechner "Intralesional interferon alfa-2b in the treatment of basal cell carcinoma", J Am Acad Dermatol 24:731-734 (1991).
Dovail et al. "Adjuvant Therapy of Stage IIIb Melanoma with Interferon Alfa-2b:Clinical and Immunological Relevance", Dermatology 191:234-239 (1995).
European Application No. 17736453.6, Extended European Search Report dated Jul. 8, 2019.
Khallouf et al. "5-Fluorouracil and Interferon-alpha Immunochemotherapy Enhances Immunogenicity of Murine Pancreatic Cancer Through Upregulation of NKG2D Ligands and MHC Class 1", Immunother 35(3):245-253 (2012).
Korthals et al. "Monocyte derived dendritic cells generated by IFN-alpha acquire mature dendritic and natural killer cell properties as shown by gene expression analysis", J Translated Medicine 5:46 (2007) (11 pages).
"U.S. Appl. No. 15/456,377; office action dated Sep. 1, 2020".
"U.S. Appl. No. 16/086,977; office action dated Sep. 3, 2020".
International Search Report and Written Opinion corresponding to International Application No. PCT/US2017/049745 dated Dec. 15, 2017.
Adams et al., "(P2-11-01) Safety and clinical activity of atezolizumab (anti-PDL1) in combination with nab-paclitaxel in patients with metastatic triple-negative breast cancer", 2015, XP002775314, 2015 San Antonio Breast Cancer Symposium, URL: http://sabcs.org/portals/sabcs2016/documents/sabcs-2015-abstracts.pdf?v=5.
Adams et al., "Phase Ib trial of atezolizumab in combination with nab-paclitaxel in patients with metastatic triple-negative breast cancer (mTNBC)" Journal of Clinical Oncology col. 34, No. 15, May 1, 2016, 4 pages.
Anonymous, "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.
Anonymous, "Atezolizumab Plus Abraxane Promising New Treatment for Triple-Negative Breast Cancer", UNM Comprehensive Cancer Center, Jan. 7, 2016, pp. 1-2.
Emens et at.: "(OT1-01-06) A phase III randomized trial of atezolizumab in combination with nab-paclitaxel as first line therapy for patients with metastatic triple-negative breast cancer (mTNBC)", 2015, XP082775313, 2015 San Antonio Breast Cancer Symposium, URL: http://sabcs.org/portals/sabcs2015/documents/sabcs-2015-abstracts.pdf?v=5.
Fabi et al, "Prospective study on nanoparticle albumin-bound paclitaxel in advanced breast cancer; clinical results and biological observations in taxane-pretreated patients", Drug Design, Development and Therapy vol. 9, Nov. 1, 2015, 7 pages.
Hamilton et al, "Nab-Paclitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.
Inman, "Atezolizumab/Nab-Paclitaxel Combo Shows High Response Rates in TNBC", OneLive, Dec. 10, 2015, 4 pages.
International Search Report and Written Opinion corresponding to International Application No. PCT/US2017/049745 dated Nov. 27, 2017.
International Search Report and Written Opinion corresponding to International Application No. PCT/US2017/050134 dated Nov. 16, 2017.
International Search Report and Written Opinion corresponding to International Application No. PCT/US2017/050137 dated Nov. 27, 2017.
Mustacchi et al, "The role of taxanes in triple-negative breast cancer: literature review", Drug Design, Development and Therapy, vol. 9, Aug. 5, 2015, 16 pages.
Nahleh et al, "Swog S0800 (NCI CDR0000636131): addition of bevacizumba to neoadjuvant nab-paclitaxel with dose-dense doxorubicin and cyclophosphamide improves pathologic complete response (pCR) rates in inflammatory or locally advanced breast cancer", Breast Cancer Research and Treatment, vol. 158, No. 3 Jul. 8, 2016, 12 pages.
Volk-Draper et al, "Novel Model for Basaloid Triple-negative Breast Cancer: Behavior In Vivo and Response to Therapy", vol. 14, No. 10, Oct. 1, 2012, 18 pages.
Anonymous "Paclitaxel Albumin-Stabilized Nanoparticle Formulation and Bevacizumab in Treating Patients With Stage IV Melanoma That Cannot Be Removed by Surgery or Gynecological Cancers", NCT02020707, ClinicalTrials.gov, Dec. 25, 2013 (13 pages).
U.S. Appl. No. 15/187,672, office action date3d Sep. 11, 2019.
U.S. Appl. No. 15/225,428, office action dated Jul. 31, 2019.
U.S. Appl. No. 15/225,428, office action dated Dec. 6, 2019.
U.S. Appl. No. 15/225,542, office action dated Jan. 14, 2020.
U.S. Appl. No. 15/286,024, office action dated Aug. 1, 2019.
U.S. Appl. No. 15/359,569; office action dated Jan. 17, 2020.
U.S. Appl. No. 15/430,411; office action dated Oct. 31, 2019.
U.S. Appl. No. 15/456,395; office action dated Aug. 14, 2019.
U.S. Appl. No. 15/456,399; office action dated Aug. 14, 2019.
U.S. Appl. No. 15/460,552; office action dated Aug. 14, 2019.
U.S. Appl. No. 15/460,699; office action dated Aug. 28, 2019.
U.S. Appl. No. 15/461,288; office action dated Aug. 28, 2019.
U.S. Appl. No. 15/675,596; office action dated Dec. 3, 2019.
U.S. Appl. No. 15/752,155; office action dated Sep. 25, 2019.
Cirstoiu-Hapca et al. "Benefit of anti-HER2-coated paclitaxel-loaded immuno-nanpoarticles in the treatment of disseminated ovarian cancer: Therapeutic efficacy and biodistribution in mice", Journal of Controlled Release 144:324-331 (2010).
European Application No. 17771005.0, Extended European Search Report dated Oct. 17, 2019.
European Application No. 17771006.8, Extended European Search Report dated Oct. 10, 2019.
International Preliminary Report on Patentability for Application No. PCT/US2017/050134 dated Mar. 21, 2019.
Liu et al. "Freeze-Drying of Proteins". In: Walkers W., Oldenhof H. (eds) Cryopreservation and Freeze-Drying Protocols. Methods in Molecular Biology (Methods and Protocols), vol. 1257. Springer, New York, NY; published online Nov. 14, 2014.
Reynolds et al. "Phase II Trial of Nanoparticle Albumin-Bound Paclitaxel, Carboplatin, and Bevacizumab in First-Line Patients with Advanced Nonsquamous Non-small Cell Lung Cancer", J Thoracic Oncology 4(12):1537-1543 (2009).
U.S. Appl. No. 15/359,569, office action dated Jul. 26, 2019.
"Concurrent Infusions", J Oncol Pract., 4(4): 171, Jul. 2008.
Abraxane® for Injectable Suspension (paclitaxel protein-bound particles for injectable suspension) (albumin-bound), [drug label], 22 pages, Sep. 2009.
Abraxis Bioscience, Inc., "Abraxane: For the adjuvant treatment of node-positive breast cancer administered sequentially to standard

(56) References Cited

OTHER PUBLICATIONS doxorubicin-containing combination chemotherapy," Oncologic Drugs Advisory Committee Meeting (available to public Aug. 4, 2006).
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(18S):8510 (Abstract).
Allen "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II, multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patients with unresectable stage IV melanoma", U.S. National Institutes of Health, 2007, 4 pages.
Anonymous, "A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: URL: https://clinicaltrials.gov/archive/NCT00434252/200703 12, dated Mar. 12, 2007. 3 pages.
U.S. Appl. No. 14/116,619, office action dated Feb. 4, 2015.
U.S. Appl. No. 14/116,619, office action dated Apr. 28, 2016.
U.S. Appl. No. 14/116,619, office action dated Sep. 10, 2015.
U.S. Appl. No. 14/432,979, office action dated Jan. 7, 2019.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016.
U.S. Appl. No. 14/882,327 office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office action dated Jan. 22, 2019.
U.S. Appl. No. 15/052,336, office action dated Feb. 9, 2018.
U.S. Appl. No. 15/052,336, office action dated Sep. 4, 2018.
U.S. Appl. No. 15/052,623, office action dated Jan. 7, 2019.
U.S. Appl. No. 15/052,623, office action dated Feb. 9, 2018.
U.S. Appl. No. 15/052,623, office action dated May 19, 2017.
U.S. Appl. No. 15/052,623, office action dated Jul. 9, 2018.
U.S. Appl. No. 15/052,623, office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/092,433; office action dated Dec. 12, 2018.
U.S. Appl. No. 15/187,672, office action dated May 31, 2018.
U.S. Appl. No. 15/187,672, office action dated Nov. 28, 2018.
U.S. Appl. No. 15/202,115, office action dated Jan. 20, 2017.
U.S. Appl. No. 15/202,115, office action dated Sep. 26, 2016.
U.S. Appl. No. 15/225,428, office action dated Aug. 14, 2018.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/331,754; office action dated Feb. 22, 2019.
U.S. Appl. No. 15/331,754; office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,536; office action dated Oct. 1, 2018.
U.S. Appl. No. 15/412,554, office action dated Sep. 27, 2018.
U.S. Appl. No. 15/412,564, office action dated Jul. 10, 2018.
U.S. Appl. No. 15/412,581; office action dated Nov. 13, 2018.
U.S. Appl. No. 15/412,596, office action dated Sep. 4, 2018.
U.S. Appl. No. 15/412,596, office action dated Dec. 27, 2018.
U.S. Appl. No. 15/412,610, office action dated Jul. 9, 2018.
U.S. Appl. No. 15/413,257; office action dated Sep. 25, 2018.
U.S. Appl. No. 15/414,526; office action dated Nov. 16, 2018.
U.S. Appl. No. 15/414,533; office action dated Nov. 19, 2018.
U.S. Appl. No. 15/414,536; office action dated Oct. 11, 2018.
U.S. Appl. No. 15/452,669, office action dated May 5, 2017.
U.S. Appl. No. 15/452,669, office action dated Nov. 16, 2017.
U.S. Appl. No. 15/452,669, office action dated Nov. 26, 2018.
Arakawa et al., "Protein-Solvent Interactions in Pharmaceutical Formulations", Pharm Res., Mar. 1991, vol. 8, Issue 3, pp. 285-291.
Armitage et al., "New approach to classifying non-Hodgkin's lymphomas: clinical features of the major histologic subtypes. Non-Hodgkin's Lymphoma Classification Project" J Clin Oncol 16, 2780-2795 (1998).
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:SII-14.
Atkins, "Interleukin-2: clinical applications" Semin Oncol., 2002, 29(3 Suppl 7):12-27.
Avastin® Bevacizumab, Roche, [drug label], 24 pages, Sep. 2008.
Baba, Oleo Science 10(1):15-18 (Jan. 2010).
Bairagi et al,. Albumin: A Versatile Drug Carrier, Austin Therapeutics, (Nov. 17, 2015) vol. 2, No. 2, p. 1021 (pp. 1-6).
Balch et al,. "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, issue 4, pp. 379-385.
Bauer et al., "Rituximab, ofatumumab, and other monoclonal anti-CD20 antibodies for chronic lymphocytic leukaemia (Review)," Cochrane Database of Systematic Reviews; Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter randomized trial for stage IIIB or IV non-small-cell lung cancer using weekly paclitaxel and carboplatin followed by maintenance weekly paclitaxel or observation"; J. Clin. Oncol., 2003, 21:2933-2939.
Bird et al., "Single-chain antigen-binding proteins", Science, Oct. 1988, 242(4877), pp. 423-426.
Boasberg et al., "Nab-paclitaxel and bevacizumab as first-line therapy in patients with unresectable stage III and IV melanoma", J Clinical Oncology, 2009, 27, No. 15S, abstract #9071.
Boasberg et al. "Phase II trial of nab-paclitaxel and bevacizumab as first-line therapy in patients with unresectable melanoma", Journal of Clinical Oncology, May 20, 2011, vol. 29, No. 15 Supp, 8543.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumeb", Clin Transl Oncol, 2007, 9;119-120.
Carson et al., "A phase 2 trial of a recombinant humanized monoclonal anti-vascular endothelial growth factor (VEGF) antibody in

(56) References Cited

OTHER PUBLICATIONS patients with malignant melanoma", Proceedings of the ASCO vol. 22, No. 2873, General Poster Session; Thirty-Ninth Annual Meeting of the American Society of Clinical Oncology, May 31-Jun. 3, 2003, Chicago, IL, 2 pages.

Celis, "Overlapping human leukocyte antigen class I/II binding peptide vaccine for the treatment of patients with stage IV melanoma: evidence of systemic immune dysfunction"; Cancer, 2007, 110(1):203-214.

Chapman et al., "Improved Survival with Vemurafenib in Melanoma with BRAF V600E Mutation", The New England Journal of Medicine, Jun. 30, 2011, vol. 364, Issue 26, pp. 2507-2516.

Chisholm et al. "Response to influenza immunization during treatment for cancer", Arch Dis Child, 2001, 84(6):496-500.

Chong et al., "Combining cancer vaccines with chemotherapy", Expert Opin Pharmacother., 2006, 6(16):2813-2820.

Cleland et al., "The Development of Stable Protein Formulations: A close lock at protein aggregation, deamidation, and oxidation", Therapeutic Drug Carrier Systems, 1993, 10(4), pp. 307-377.

Colman, "Effects of amino acid sequence changes on antibody-antigen interactions," Research in Immunology (145 (1):33-36, (1994).

Davis, "Affinity separation of antibody-toxin conjugate from albumin-stabilized formulation", Am Biotechnol Lab., 12(4):60-64, Mar. 1994.

Degrasse, "A Single-Stranded DNA Aptamer That Selectively Binds to *Staphylococcus aureus* Enterotoxin B", PLoS One, 2012, 7(3) e33410, pp. 1-7.

Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.

Deniirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.

Denardo et al., "Inflammation and breast cancer. Balancing immune response: crosstalk betwen adaptive and innate immune cells during breast cancer progression", Breast Cancer Res., 2007, 9(4):212.

Desai et al., "Enhanced antitumor activity and safety of albumin-bound nab-docetaxelversus polysorbate 80-based docetaxel", Eur. J. Cancer, Suppl.; 18th Symposium on molecular targets and cancer therapeutics; Prague, Czech Republic; Nov. 7 -10, 2006, vol. 4, No. 12, Nov. 2006 *Nov. 2006), p. 49.

Desai et. al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.

Deweers et al., "Daratumumab, a novel therapeutic human CD38 monoclonal antibody, induces killing of multiple myeloma and other hematological tumors", J. Immunol., 186(3): 1840-1848, Feb. 1, 2011.

Dudek et al., "Autologous large multivalent immunogen vaccine in patients with metastatic melanoma and renal cell carcinoma", Am. J. Clin. Oncol., Apr. 1, 2008, 31(2):173-181.

Edison, "MorphoSys," 16 pages (Aug. 8, 2013).

Elbayoumi et al., "Tumor-Targeted Nanomedicines: Enhanced Antitumor Efficacy In vivo of Doxorubicin-Loaded, Long-Circulating Liposomes Modified with Cancer-Specific Monoclonal Antibody", Clin Cancer Res., 2009, 15(6):1973-1980.

Ellyard et al., "Th2-mediated anti-tumour immunity: friend or foe?", Tissue Antigens, 2007, 70(1):1-11.

Elsadek et al., "Impact of albumin on drug delivery—New applications on the horizon" J of Controlled Release, 2011, 1-25.

Elst et al, "Epidermal Growth Factor Receptor Expression and Activity in Acute Myeloid Leukemia", Blood 116:3144 (2010), abstract.

European Application No. 08743903.0, Extended European Search Report dated Jan. 24, 2011.

European Application No. 09774506.1, Extended European Search Report dated Mar. 22, 2012.

European Application No. 12781802.9, Extended European Search Report dated Dec. 18, 2014.

European Application No. 13843209.1. Extended European Search Report dated Sep. 5, 2016.

European Application No. 15806443.6, Extended European Search Report dated Dec. 11, 2017.

European Application No. 15809075.3, Extended European Search Report dated Dec. 21, 2017.

Ferrara et al., "The biology of VEGF and its receptors", Nat. Med., 2003, 9:669-676.

Flaherty et al., "Final Results of E2603: a double-blind, randomized phase III trial comparing carboplatin (C)/paclitaxel(P) with or without sorafenib(S) in metastatic melanoma", J. Glin Oncol., 2010, 28:15s (suppl: abstr 8511).

Flores et al., "Novel oral taxane therapies: recent Phase I results", Clin. Invest, vol. 3, No. 4, Apr. 1, 2013 (Apr. 1, 2013), pp. 333-341, XP055426671, UK, ISSN: 2041-6792, DOI: 10.4155/cli.13.18.

Folkman, "Angiogenesis in cancer, vascular, rheumatoid and other disease", Nat. Med., 1995, 1, 27-31.

Fricke et al., "Vascular endothelial growth factor-trap overcomes defects in dendritic cell differentiation but does not improve antigen-specific immune responses", Clin, Cancer Res., 2007, 13:4840-4848.

Gabrilovich et al., "Production of vascular endothelial growth factor by human tumors inhibits the functional maturation of dendritic cells", Nat. Med., 1996, 2: 1096-1103.

Gao et al., "In vivo cancer targeting and imaging with semiconductor quantum dots", Nat Biotech, 2004, 22(8):969-976.

Gogas et al., "Chemotherapy for metastatic melanoma: time for a change?", Cancer, 2007, 109(3): 455-464.

Golay et al., "Mechanism of action of therapeutic monoclonal antibodies: promises and pitfalls of in vitro and in vivo assay," Arch. Biochem. Biophys. 526(2):146-153 (2012).

Graells et al., Overproduction of VEGF165 concomitantly expressed with its receptors promotes growth and survival of melanoma cells through MAPK and P13K signaling, J. Invest. Dermatol., 2004, 123;1151-1161.

Gupta et al., "Ofatumumab, the first human anti-CD20 monoclonal antibody for the treatment of B cell hematologic malignancies," Ann. N.Y. Acad. Sci., 1263, pp. 43-56 (Jul. 25, 2012).

Haley et al., "Nanoparticles for drug delivery in cancer treatment", Urol. Oncol.: Seminars and Original Invest., 2008, 26:57-64.

Hara, "What is anti-HER2 antibody tubulin polymerization inhibitor complex T-DM1?," Pharm. Monthly 56(5):734-739 (May 2014).

Harlow et al., Antibodies: A Laboratory Manual, Gold Spring Harbor Laboratory, New York, 1988 (9 pages).

Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 385-394.

Hauschild et al., "Individualized therapy of disseminated cancer using malignant melanoma as a model",Cancer and Metastasis Reviews, 2006, 25(2): 253-256.

Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.

Hegde et al, "Predictive Impact of Circulating Vascular Endothelial Growth Factor in Four Phase III Trials Evaluating Bevacizumab," Clinical Cancer Research; Feb. 15, 2013 (Feb. 15, 2013) vol. 19, pp. 929-937.

Hersh et al., "A Phase 2 Clinical Trial of nab-Paclitaxel in Previously Treated and Chemotherapy-Naive Patients With Metastatic Melanoma", Cancer, Jan. 1, 2010, 116:155, pp. 155-163.

Hersh et al., "A randomized, controlled phase III trial of nab-Paclitaxel versus dacarbazine in chemotherapy-naive patients with metastatic melanoma", Ann Oncol, 2015, epub Sep. 26, 2015.

Hersh et al., "Open-label, multicenter, phase II trial of ABI-007 in previously treated, and previously untreated patients with metastatic malignant melanoma", J. Clin. Oncol., 2005, 23(16S);7558 (Abstract).

I ---.

(56) References Cited

OTHER PUBLICATIONS

Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Hood et al., Immunology, 1984, Benjamin, N.Y., 2nd edition.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites: Recovery of specific activity in an anti-digoxin single-chain Fv analogue produced in *Escherichia coli*", Proc. Natl. Acad. Sci, USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
International Preliminary Report on Patentability for Application No. PCT/US2008/057025, dated Sep. 15, 2009.
International Preliminary Report on Patentability for Application No. PCT/US2009/049511, dated Jan. 5, 2011.
International Preliminary Report on Patentability for Application No. PCT/US2012/037137, dated Nov. 12, 2013.
International Preliminary Report on Patentability for Application No. PCT/US2013/062638, dated Apr. 16, 2015.
International Preliminary Report on Patentability for Application No. PCT/US2015/035505, dated Dec. 22, 2016.
International Preliminary Report on Patentability for Application No. PCT/US2015/035515, dated Dec. 29, 2016.
International Preliminary Report on Patentability for Application No. PCT/US2015/054295 dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442, dated Oct. 4, 2018.
International Preliminary Report on Patentability for Application No. PCT/US2017/023443, dated Oct. 4, 2018.
International Preliminary Report on Patentability for Application PCT/US2016/026267, dated Apr. 10, 2018.
International Preliminary Report on Patentability for Application PCT/US2017/017553, dated Aug. 23, 2018.
International Search Report and Written Opinion for Application No. PCT/US2008/057025, dated Jul. 1, 2008.
International Search Report and Written Opinion for Application No. PCT/US2009/049511, dated Feb. 2, 2010.
International Search Report and Written Opinion for Application No. PCT/US2012/037137, dated Sep. 28, 2012.
International Search Report and Written Opinion for Application No. PCT/US2013/062636, dated Jan. 23, 2014.
International Search Report and Written Opinion for Application No. PCT/US2015/035505, dated Nov. 24, 2015.
International Search Report and Written Opinion for Application No. PCT/US2015/035515, dated Sep. 21, 2015.
International Search Report and Written Opinion for Application No. PCT/US2015/054295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2016/047641, dated Oct. 31, 2016.
International Search Report and Written Opinion for Application No. PCT/US2017/012580, dated Mar. 17, 2017.
International Search Report and Written Opinion for Application No. PCT/US2017/017553, dated Feb. 10, 2017.
International Search Report and Written Opinion for Application No. PCT/US2017/045643, dated Oct. 25, 2017.
International Search Report and Written Opinion for Application No. PCT/US2017/050355 dated Jan. 30, 2018.
Jaime et al., "Paclitaxel antibody conjugates and trehalose for preserving the immunological activity after freeze-drying," Curr Med Chem, 2004, 11(4):439-46 Abstract Only.
Jain et al., "Delivering nonomedicine to solid tumors", Nature Reviews Clinical Oncology, Nov. 2010, 7, pp. 653-664.
Jain et al., "Normalizing tumor vasculature with anti-angiogenic therapy: a new paradigm for combination therapy," Nat. Med. 7(9):987-989 (2001).
Jain, "Normalization of tumor vasculature: an emerging concept in antiangiogenic therapy," Science 307(5706):58-62 (2005).
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paclitaxel-induced apoptosis," Mol. Cancer Ther. 2(11):1183-93 (2003).
Jiang et al., "Regulation of Immune Responses by T Cells", N Engl Med., 2006, 354(11): 1166-1176.
Jin et al., "Paclitaxel-loaded nanoparticles decorated with anti-CD133 antibody: a targeted therapy for liver cancer stem cells," J. Nanopart. Res. 2014, 16:2157 (2014).
Jin et al: "Docetaxel-loaded PEG-albumin nanoparticles with improved antitumor efficiency against non-small cell lung cancer", Oncology Reports vol. 36, No. 2, Aug. 8, 2016 (Aug. 8, 2016), pp. 871-876, XP055425487, ISSN: 1021-335X, DOI: 10.3892/or.2016.4863.
Julien et al, "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-small cell lung carcinoma patients", Lung Cancer, 2008, 59(1):41-47.
Kelly et al. "Shape-Specific, Monodisperse Nano-Molding of Protein Particles," J. Am. Chem. Soc. 130:5438-5439 (2008).
Kikuchi et al., "Vascular endothelial growth factor and dendritic cells in human squamous cell carcinoma of the oral cavity", Anticancer Res., 2006, 26(3A):1833-1848.
Kim et al., "A dual target-directed agent against interleukin-6 receptor and tumor necrosis factor a ameliorates experimental arthritis", Scientific Rep. 6:20150 (2016).
Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncoloy official journal of the American Society of Clinical Oncology, Jan. 1, 2012, vol. 30, No. 1, pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.
Korman et al., "Tumor immunotherapy: preclinical and clinical activity of anti-CTLA4 antibodies", Curr Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.

(56) References Cited

OTHER PUBLICATIONS

Kottschade et al., "A Randomized Phase 2 Study of Temozolomide and Bevacizumab or nab-Paclitaxel, Carboplatin, and Bevacizumab in Patients with Unresectable Stage IV Melanoma",Cancer, 2013, vol. 119, Issue 3, pp. 586-592.
Kratz et al., "Serum proteins as drug carriers of anticancer agents: a review", Drug Deliv., 5(4):281-299, 1998.
Kratz, "Albumin as a drug carrier: design of prodrugs, drug conjugates and nanoparticles" J Control Release, 132(3):171-183, Epub May 17, 2008.
Krishnan et al., "Programmed death-1 receptor and interleukin-10 in liver transplant recipients at high risk for late cytomegalovirus disease".
Kukowska-Latallo et al., "Nanoparticle Targeting of Anticancer Drug Improves Therapeutic Response in Animal Model of Human Epithelial Cancer", Cancer Res, 2005, 65(12):5317-5324.
Kumar et al., ThI/Th2 cytokine imbalance in meningioma, anaplastic astrocytoma and glioblastoma multiforme patients, Oncol. Ren., 2006, 15(6):1513-1516.
Lanzavecchia et al., "The use of hybrid hybridomas to target human cytotoxic T lymphocytes", Eur. J. Immunol., 1987, 17, pp. 105-111.
Lau et al., "Is inhibition of cancer angiogenesis and growth by paclitaxel schedule dependent?", Anti-Cancer Drugs, 2004, 15:871-875.
Lee et al., "The co-delivery of paclitaxel and Herceptin using cationic micellar nanoparticles", Biomaterials vol. 30, No. 5, Feb. 1, 2009, pp. 919-927.
Lei et al., "Comparing cellular uptake and cytotoxicity of targeted drug carriers in cancer cell lines with different drug resistance mechanisms", Nanomed: Nanotech, Biol, and Med., 2011, 7:324-332.
Lev et al., "Dacarbazine causes transcriptional up-regulation of interleukin 8 and vascular endothelial growth factor in melanoma cells: a possible escape mechanism from chemotherapy", Mol. Cancer Ther., 2003, 2:753-763.
Lev et al., "Exposure of melanoma cells to dacarbazine results in enhanced tumor growth and metastasis in vivo", J. Clin. Oncol., 2004, 22:2092-2100.
Liang et al., "IFN-alpha regulates NK cell cytotoxicity through STAT1 pathway," Cytokine, Aug. 13, 2003 (Aug. 13, 2013), vol. 23, pp. 190-199.
Lin, "Salmon Calcitonin: Conformational Changes and Stabilizer Effects", AIMS Biophysics, 2015, 2(4): 695-723.
Lloyd et al. "Modelling the human immune response: performance of a 1011 human antibody repertoire against a broad panel of therapeutically relevant antigens", Protein Eng. , Design & Selection 22(3):159-168 (2009).
Lundin et al., "Phase 2 study of alemtuzumab (anti-CD52 monoclonal antibody) in patients with advanced mycosis fungoides/Sezary syndrome", Blood (2003) vol. 101, No. 11, pp. 4267-4272.
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Marcoval et al., "Angrogenesis and malignant melanoma. Angiogenesis is related to the development of vertical (tumorigenic) growth phase", J. Cutan. Pathol 1997, 24:212-218.
Markovic et al., "A phase II study of ABT-510 (thrombospondin-1 analog) for the treatment of metastatic melanoma", Am. J. Clin. Oncol., 2007, 30(3):303-309.
Markovic et al., "A reproducible method for the enumeration of functional ( cytokine producing) versus non-functional peptide-specific cytotoxic T lymphocytes in human peripheral blood", Clin. Exo. Immunol., 2006, 145:438-447.
Markovic et al., "Peptide vaccination of patients with metastatic melanoma: improved clinical outcome in patients demonstrating effective immunization", Am J Clin Oncol., 2006, 29(4):352-360.
Matejtschuk, "Lyophilization of Proteins", Methods in Molecular Biology, Cryopreservation and Freeze-Drying Protocols, Second Edition, Edited by: J.G. Day and G.N. Stacey, Humana Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.
Mayo Clinic, "Paclitaxel Albumin-Stabilized Nanoparticle Formulation and Bevacizurnab in Treating Patients With Stage IV Melanoma That Cannot Be Removed by Surgery", Dec. 19, 2013, ClinicalTrials.gov., URL: https://www.clinicaltrials.gov/ct2/show/NCT02020707 (Four (4) pages).
McElroy et al., "Imaging of Primary and Metastatic Pancreatic Cancer Using a Fluorophore-Coniugated Anti-CA19-9 Antibody for Surgical Navigation", World J Surg, 2008, 32: 1057-1066.
Meadows et al. "Anti-VEGF Therapies in the Clinic," Cold Spring Harbor Perspectives in Medicine, Oct. 1, 2012 (Oct. 1, 2012), vol. 2, pp. 1-27.
Melcher, "Recommendations for influenza and pneumococcal vaccinations in people receiving chemotherapy", Clin Oncol (R Coll Radion), 2005, 17(1): 12-15.
Merchan et al., "Increased endothelial uptake of paclitaxel as a potential mechanism for its antiangiogenic effects: potentiation by Cox-2 inhibition", Int. J. Cancer, 2005, 113, pp. 490-498.
Mezzaroba et al., "New potential therapeutic approach for the treatment of B-Cell malignancies using chlorambucil/Hydroxychloroquine-Loaded Anti-CD20 Nanoparticles", Sep. 2103, PLoS ONE vol. No. 8, Issue 9 pp. 1-10, e74216.
Middleton et al., "Randomized phase III study of temozolomide versus dacarbazine in the treatment of patients with advanced metastatic malignant melanoma", J. Clin. Oncol, 2000, 18, pp. 158-166.
Miller et al., "Paclitaxel plus Bevacizumab versus Paclitaxel Alone for Metastatic Breast Cancer," N Engl. J Med., (2007) vol. 357:2666-2676.
Mimura et al., Vascular endothelial growth factor inhibits the function of human mature dendritic cells mediated by VEGF receptor-2, Cancer Immunol Immunother., 2007, 56(6). pp. 761-770.
Mirtsching et al., "A Phase II Study of Weekly Nanoparticle Albumin-Bound Paclitaxel With or Without Trastuzumab in Metastatic Breast Cancer", Clinical Breast Cancer; 2011, 11(2):121-128.
Mocellin et al., "Cytokines and immune response in the tumor microenvironment", J Immunother., 2001, 24(5), pp. 392-407.
Motl, "Bevacizumab in combination chemotherapy for colorectal and other cancers", Am. J. Health-Svst. Pharm , 2005, 62, pp. 1021-1032.
Nevala et al, "Abstract B77: Targeted nano-immune conjugates to melanoma: Preclinical testing of bevacizumab targeted nab-paclitaxel", Cancer Immunology Research, vol. 3, Oct. 1, 2015, 3 pages.
Nevala et al, "Antibody-targeted paclitaxel loaded nartopairtcles for the treatment of CD20 B-cell lymphoma", Scientific Reports, vol. 7, Apr. 5, 2017, 9 pages.
Nevala et al, "Antibody-Targeted Chemotherapy for the Treatment Melanoma", Cancer Research, vol. 76, No. 13, Jul. 1, 2016, pp. 3954-3964.
Nevala et al, "Targeted nano-immune conjugates to melanoma: Preclinical testing of bevacizumab targeted nab-paclitaxel", Proceedings of the AACR Special Conference: Tumor Immunology and Immunotherapy: A New Chapter, Dec. 1, 2014, 2 pages.
Ng et al., "Influence of formulation vehicle on metronomic taxane chemotherapy: albumin-bound versus cremophor EL-based paclitaxel", Clin. Cancer Res., 2006, 12, pp. 4331-4338.
Ng et al., "Taxane-mediated antiangiogenesis in vitro: influence of formulation vehicles and binding proteins", Cancer Res., 2004, 64, pp. 821-824.
Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.
Nishida et al, English Translation of "Clinical Trials of New Drugs Cytotoxic Effect against Multiple Myeloma with High Expression

(56) References Cited

OTHER PUBLICATIONS of a CD38 Antigen and a Human CD38 Monoclonal Antibody Daratumumab:CD38 Antigen", history of Medicine, Sep. 29, 2012. vol. 242, No. 13, pp. 1176-1181.

Oku et al., "Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts", Cancer Res., 1998, 58, pp. 4185-4192.

Ortaldo et al., "Effects of several species of human leukocyte interferon on cytotoxic activity o fNK cells and monocytes," International Journal of Cancer, Mar. 15, 1983 (Mar. 15, 1983) vol. 31, No. 3, pp. 285-289.

Ouichi, "Antibody delivery—from basics to clinical test—Clinical development of antibody-drug conjugate," Drug Deliv. Sys. 28(5):424-429 (2013).

Parikh et al., "The vascular endothelial growth factor family and its receptors", Hematol. Oncol. Clin. N. Am., 2004, 18, pp. 951-971.

Park et al., "Anti-HER2 Immunoliposomes: Enhanced Efficacy Attributable to Targeted Delivery", Clin. Cancer Res., 2002, 8, pp. 1172-1181.

Parker et al., "Targeting CII Cells Using Rituximab-Conjugated Surface Enhanced Raman Scattering (SERS) Gold Nanoparticles," Blood vol. 116, No. 21, Nov. 1, 2010, pp. 1109.

Perez et al., "Phase 2 Trial of Carboplatin, Weekly Paclitaxel and Biweekly Bevacizumab in Patients with Unresectable Stage IV Melanoma", Cancer, 2009, vol. 115, Issue 1, pp. 119-127.

Petrelli et al., "Targeted Delivery for Breast Cancer Therapy: the History of Nanoparticle-Albumin-Bound Paclitaxel," Expert Opinion on Pharmacotherapy Jun. 1, 2010 (Jun. 1, 2010), vol. 11, pp. 1413-1432.

Pikal., "Freeze-drying of proteins, Part II. Formulation selection", Biopharm, 1990, 9, pp. 26-30.

Polak et al., "Mechanisms of local immunosuppression in cutaneous melanoma", Br J Cancer, 2007, 96(12), pp. 1879-1687.

Porrata et al., "Early lymphocyte recovery predicts superior survival after autologous hematopoietic stem cell transplantation in multiple myeloma or non-Hodgkin lymphoma", Blood, 2001, 98(3), pp. 579-585.

Porrata et al., "Timely reconstitution of immune competence affects clinical outcome following autologous stem cell transplantation", Clin Exp Med., 2004, 4(2):78-85.

Powell et al., "Adoptive transfer of vaccine-induced peripheral blood mononuclear cells to patients with metastatic melanoma following lymphodepletion", J Immunol., 2006, 177(9), pp. 6527-6539.

Pries et al., "Cytokines in head and neck cancer", Cytokine Growth Factor Rev., 2006 17(3), pp. 141-146.

Qu Na et al: "Cabazitaxel-loaded human serum albumin nanoparticies as a therapeutic agent against prostate cancer", International Journal of Nanomedicine, vol. 11, Jul. 26, 2016 (Jul. 26, 2016), pp. 3451-3459.

Ranieri et al., "Vascular endothelial growth factor (VEGF) as a target of bevacizumab in cancer: from the biology to the clinic", Curr. Med. Chem., 2006, 13, 1845-1857.

Rao et al., "Combination of Paclitaxel and Carboplatin as Second-Line Therapy for Patients with Metastatic Melanoma", Cancer, Jan. 15, 2006, vol. 106, No. 2, pp. 375-382.

Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.

Rosenberg et al., "Tumor progression can occur despite the induction of very high levels of self/tumor antigen-specific CD8+ T cells in patients with melanoma", J. Immunol., 2005, 175(9), pp. 6169-6176.

Roy et al., "Tumor associated release of interleukin-10 alters the prolactin receptor and down-regulates prolactin responsiveness of immature cortical thymocytes", J Neuroimmunol., 2007, 186(1-2), pp. 112-120.

Rudikoff et al., "Single amino acid substitution altering antigen-binding specificity," Proc Natl Aced Sci USA 1982 vol. 79 pp. 1979-1983.

Rudnicka et al., "Rituximab causes a polarization of B cells that augments its therapeutic function in NK-cell-mediated antibody-dependent cellular cytotoxicity", Blood, 2013, 121(23):4694-4702.

Sadat et al., "Nano-pharmaceutical Formulations for Targeted Drug Delivery against HER2 in Breast Cancer" Current Cancer Drug Targets, 2015, 15(1):71-86.

Salven et al., "Enhanced expression of vascular endothelial growth factor in metastatic melanoma", Br. J. Cancer, 1997, 76(7), pp. 930-934.

Samaranayake et al., "Modified taxols. 5.1 Reaction of taxol with electrophilic reagents and preparation of a rearranged taxol derivative with tubulin assembly activity", J. Org. Chem., vol. 56, 1991, pp. 5114-5119.

Sandler et al., "Paclitaxel-carboplatin alone or with bevacizumab for non-small-cell lungcancer", N. Engl. J. Med., 2006, 355:2542-2550.

Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.

Schrama et al. "Antibody targeted drugs as cancer therapeutics", Nature Reviews 5:147-159 (2006).

Sester et al., "Differences in CMV-specific T-cell levels and long-term susceptibility to CMV infection after kidney, heart and lung transplantation", Am J Transplant., 5(6):1483-1489, Jun. 2005.

Soda et al., "Latest topics of new medicine Albumin-bound paclitaxel," Mol. Respiratory Dis. 17(1):100-103 (Mar. 1, 2013).

Srivastava et al., "Angiogenesis in cutaneous melanoma: pathogenesis and clinical implications", Microsc. Res. Tech., 2003, 60;208-224.

Stancovski et al., "Mechanistic aspects of the opposing effects of monoclonal antivodies to the ERBB2 receptor on tumor growth," Proc Natl Acad Sci USA, 88: 8691-8695, (1991).

Streit et al., "Angiogenesis, lymphangiogenesis, and melanoma metastasis", Oncogene, 2003, 22, pp. 3172-3179.

Taieb et al., "Chemoimmunotherapy of tumors: Cyclophosphamide synergtizes with exoxome based vaccines", J. lmmunol., Mar. 1, 2006, 176(5):2722-2729.

Tao et al., "Inhibiting the growth of malignant melanoma by blocking the expression of vascular endothelial growth factor using an RNA interference approach", Br. J. Dermatol., 2005, 153:715-724.

Tas et al., "Circulating serum levels of angiogenic factors and vascular endothelial growth factor receptors 1 and 2 in melanoma patients", Melanoma Res., 2006, 16:405-411.

Terheyden et al., "Anti-vascular endothelial growth factor antibody bevacizumab in conjunction vtrith chemotherapy in metastasizing melanoma", J Cancer Res Olin Oncol, 2007, 133(11), pp. 897-901.

Terui, English Translation of Molecular-Targeted Therapy for Cancer: Progresses and Challenges, "Daratumumab, Antibody Drug against Myeloma", Pharma Med., Nov. 10, 2013, vol. 31, No. 11, p. 27-30.

Ugurei et al., "Increased serum concentration of angiogenic factors in malignant melanoma patients correlates with tumor progression and survival", J. Clin. Oncol., 2001, 19:577-583.

Vacca et al., "Docetaxel versus paclitaxel for antiangiogenesis", J. Hematother. Stem Cell Res., 2002, 11:103-118.

Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.

Vence et al., "Circulating tumor antigen-specific regulatory T cells in patients with meastatic melanoma", Proc Natl Acad Sci USA, 2007, 104(52), pp. 20884-20889.

Vishnu et al., "Safety and Efficacy of nab-Paclitaxel in the Treatment of Patients with Breast cancer," Breast Cancer: Basic and Clinical Research, 2011, vol. 5, pp. 53-65.

(56) References Cited

OTHER PUBLICATIONS

Volk et al., "Nab-paclitaxel efficacy in the orthotopic model of human breast cancer is significantly enhanced by concurrent antivascular endothelial growth factor A therapy," Neoplasia 10(6):613-623 (2008).
Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.
Walker et al., "Monitoring immune responsesn cancer patients receiving tumor vaccines", Int Rev Immunol., 2003, 22(3-4):283-319.
Wang et al., "Biofunctionalized targeted nanoparticles for therapeutic applications", Expert Opin. Biol. Ther., 2008, 8(8): 1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-19.
Washington University School of Medicine "Phase I/II Study of Abraxane in Recurrent and Refractory Lymphoma", ClinicalTrials.gov, Dec. 6, 2016, 7 pages.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.
Wu et al., "Aptamers: Active Targeting Ligands for Cancer Diaonosis and Therapy", Theranostics, 2015, 5(4):322-344.
Yardley et al., "A pilot study of adluvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.
Yu et al., "Interaction between bevacizumab and murine VEGF-A: a reassessment," Invest. Ophthalmol. Visual Sci. 49(2): 522-5Z7, Feb. 2008.
Yuan et al., "Vascular Permeabiiity in a Human Tumor Xenograft: Molecular Size Dependence and Cutoff Size", Cancer Research, Sep. 1, 1995, 55, pp. 3752-3756.
Yuan et al., "Time-dependent vascular regression and permeability changes in established human tumor xenografts induced by an anti-vascular endothelial growth factor/vascular permeability factor antibody," Proc. Natl. Acad. Sci. USA 93(25):14765-14770 (1996).
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.
Anonymous, "Phase I/II Study of Abraxane in Recurrent and Refractory Lymphoma", NCT01555853, ClinicalTrials.gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/412,581, office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533; office action dated Mar. 8, 2019.
U.S. Appl. No. 15/430,411, office action dated May 1, 2019.
U.S. Appl. No. 15/456,377; office action dated Mar. 19, 2019.
U.S. Appl. No. 15/456,382; office action dated Mar. 18, 2019.
U.S. Appl. No. 15/456,391; office action dated Mar. 15, 2019.
U.S. Appl. No. 15/456,395; office action dated Mar. 28, 2019.
U.S. Appl. No. 15/456,399, office action dated Mar. 28, 2019.
U.S. Appl. No. 15/460,552; office action dated Apr. 1, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharmaceutical Technology Lyophilization. pp. 10-18 (2004).
Cheng et al. Molecularly targeted drugs for metastatic colorectal cancer. Drug Des Devel Ther. Nov. 1, 2013;7; 1315-22 (Year: 2013).
Coiffier "The Role of Rituximab in Lymphomas", Rev. Bras. Hematol. Hemoter., 2002, vol. 24, No. 3, ISSN: 1516-8484 (6 pages).
Edwards et al. The Remarkable Flexibility of the Human Antibody Repertoire; Isolation of Over One Thousand Different Antibodies to a Single Protein, BLyS, J. Mol. Biol 334:103-118 (2003).
European Application No. 18837869.3, Extended European Search Report dated Apr. 4, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability for Application No. PCT/US2017/050137, dated Mar. 21, 2019.
International Search Report and Written Opinion for Application No. PCT/US2017/023442, dated Jun. 16, 2017.
International Search Report and Written Opinion for Application No. PCT/US2017/023443, dated Jul. 11, 2017.
Iqbal et al, Anti-Cancer Actions of Denosumab. Curr Osteoporos Rep. Dec. 2011;9(4): 173-6. (Year: 2011).
Matthay et al. Promising therapeutic targets in neuroblastoma. Clin Cancer Res. May 15, 2012;18(10):2740-53. (Year: 2012).
Package Insert, Campath® (Alemtuzumab). Millennium and ILEX Partners, LP, 13 pages, available May 2001.
Reck et al, "Ipilimumab in combination with paclitaxel and carboplatin as first-line therapy in extensive-disease-small-cell lung cancer results from a randomized, double-blind, multicenter phase 2 trial", Ann Oncol. 24(1):75-83 (2013).
Robak, T. Emerging monoclonal antibodies and related agents for the treatment of chronic lymphocytic leukemia. Future Oneal. Jan. 2013;9(1):69-91. Abstract Only. (Year: 2013).
Verma et al. "Effect of surface properties on nanoparticle-cell interactions", Small. 6(1 ): 12-21. (2010).
U.S. Appl. No. 15/225,542; office action dated Jul. 30, 2020.
U.S. Appl. No. 15/286,024; office action dated Feb. 10, 2020.
U.S. Appl. No. 15/286,024, office action dated Jul. 29, 2020.
U.S. Appl. No. 15/359,569; office action dated Aug. 10, 2020.
U.S. Appl. No. 15/430,411, office action dated Apr. 17, 2020.
U.S. Appl. No. 15/452,669; office action dated Mar. 3, 2020.
U.S. Appl. No. 15/456,377; office action dated Mar. 12, 2020.
U.S. Appl. No. 15/456,391; office action dated Feb. 4, 2020.
U.S. Appl. No. 15/460,699; office action dated Mar. 3, 2020.
U.S. Appl. No. 15/461,288; office action dated Feb. 28, 2020.
U.S. Appl. No. 15/675,596; office action dated May 28, 2020.
U.S. Appl. No. 15/752,155; office action dated Feb. 7, 2020.
U.S. Appl. No. 16/328,146; office action dated Feb. 26, 2020.
U.S. Appl. No. 16/328,146; office action dated Jul. 28, 2020.
Barua et al. "Particle shape enhances specificity of antibody-display nanoparticles", PNAS 110(9):3270-3275 (2013).
Chuang et al. "Recombinant human serum albumin", Drugs Today 43(8):547-561 (2007) (Abstract Only) (2 pages).
European Application No. 17750912.2 Extended European Search Report dated Jan. 2, 2020.
Miele et al. "Albumin-bound formulation of paclitaxel (Abraxane® ABI-007) in the treatment of breast cancer", International Journal of Nanomedicine 4:99-105 (2009).
Warner et al. "Alemtuzumab use in relapsed and refractory chronic lymphocytic leukemia: a history and discussion of future rational use", Ther Adv Hematol 3(6):375-389 (2012).
Zhao et al. "Abraxane, the Nanoparticle Formulation of Paclitaxel Can Induce Drug Resistance by Ip-Regulation of P-gp", PLoS One 10(7):e0131429 (2015) (19 pages).

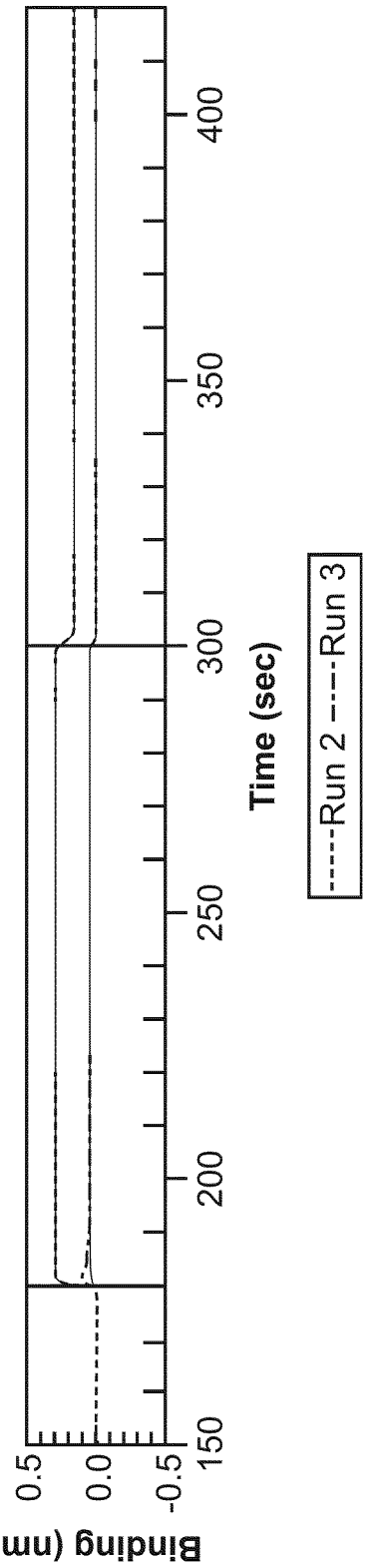

METHODS AND COMPOSITIONS FOR TARGETING T-CELL CANCERS

CROSS REFERENCE TO RELATED APPLICATIONS

This application is a 35 U.S.C. § 371 national phase application of PCT Application PCT/US2017/049745 filed Aug. 31, 2017, which claims the benefit of the priority date of U.S. Provisional Application No. 62/382,635, filed Sep. 1, 2016; the entire contents of each of which are incorporated by reference herein in its entirety.

FIELD OF THE INVENTION

This application relates to novel compositions of binding agents and carrier proteins, and methods of making and using the same, in particular, as a T cell cancer therapeutic.

BACKGROUND

Chemotherapy remains a mainstay for systemic therapy for many types of cancer, including melanoma. Most chemotherapeutic agents are only slightly selective to tumor cells, and toxicity to healthy proliferating cells can be high (Allen T M. (2002) Cancer 2:750-763), often requiring dose reduction and even discontinuation of treatment. In theory, one way to overcome chemotherapy toxicity issues as well as improve drug efficacy is to target the chemotherapy drug to the tumor using antibodies that are specific for proteins selectively expressed (or overexpressed) by tumors cells to attract targeted drugs to the tumor, thereby altering the biodistribution of the chemotherapy and resulting in more drug going to the tumor and less affecting healthy tissue. Despite 30 years of research, however, specific targeting rarely succeeds in the therapeutic context.

Conventional antibody dependent chemotherapy (ADC) is designed with a toxic agent linked to a targeting antibody via a synthetic protease-cleavable linker. The efficacy of such ADC therapy is dependent on the ability of the target cell to bind to the antibody, the linker to be cleaved, and the uptake of the toxic agent into the target cell. Schrama, D. et al. (2006) Nature reviews. Drug discovery 5:147-159.

Antibody-targeted chemotherapy promised advantages over conventional therapy because it provides combinations of targeting ability, multiple cytotoxic agents, and improved therapeutic capacity with potentially less toxicity. Despite extensive research, clinically effective antibody-targeted chemotherapy remains elusive: major hurdles include the instability of the linkers between the antibody and chemotherapy drug, reduced tumor toxicity of the chemotherapeutic agent when bound to the antibody, and the inability of the conjugate to bind and enter tumor cells. In addition, these therapies did not allow for control over the size of the antibody-drug conjugates.

There remains a need in the art for antibody-based cancer therapeutics that retain cytotoxic effect for targeted drug delivery to provide reliable and improved anti-tumor efficacy over prior therapeutics.

In addition, as to any therapeutic application, there also remains a need for the composition to be stable in its physical, chemical and biological properties.

T-cell lymphomas ("TCL") are a heterogeneous group of blood cancers that account for approximately 15% of lymphomas. Every year, there are about 6,500 new cases of TCL in the United States. TCLs include peripheral T-cell lymphoma, anaplastic large cell lymphoma, cutaneous T-cell lymphoma, adult T-cell leukemia/lymphoma, lymphoblastic lymphoma, et al. Studies show that TCL can affect both children and adults, though in some subtypes of TCL, mainly teenagers and children are affected by this blood disease, e.g. lymphoblastic lymphoma. Patients with TCL present themselves with swollen lymph nodes, high-grade lesions, and systemic symptoms, e.g., severe rash, fever, and fatigue.

TCL patients were traditionally treated with the same chemotherapies (e.g., anthracyclines) as for those with B-cell lymphomas. Compared to their efficacies against B-cell lymphomas, however, the anthracycline-based regimens have not been effective in increasing the survival rates for the TCL patients. Vose J, et al., J Clin Oncol. 2008; 26(25):4124-30. The anthracycline-based regimens are accompanied with lower response rates and shorter times to progression for the TCL patients. Given the poor outcomes with traditional chemotherapy, non-anthracycline based therapeutic regimens are greatly needed for TCL patients.

Therefore, there is a need for a more effective composition or immunotherapy to treat the T-cell cancers with minimal or no side effects.

SUMMARY OF THE INVENTION

This disclosure is related to a nanoparticle composition that comprises nanoparticles having an outer surface, wherein each of the nanoparticles comprises: a carrier protein, a binding agent with an antigen-binding portion targeting an antigen expressed on a T-cell, and a therapeutically effective amount of a therapeutic agent. In one aspect, the binding agent is capable of binding to an antigen expressed on a T-cell or a T-cell cancer (e.g., OKT3) while, at the same time, reducing or eliminating the serious side effects associated with the immunogenic and mitogenic potential limits of the antibody (e.g., OKT3). Accordingly, the nanoparticles as described herein are thus a significant improvement compared to the conventional ADCs having serious side effects and/or toxicity.

Antibody-based therapy has emerged as a new therapeutic option for lymphoma patients. For example, a monoclonal antibody, rituximab (Rituxan®), has been used in treating B-cell lymphoma with significantly improved clinical outcomes. For the T-cell neoplasm, a number of antibodies have shown their efficacies. Among them, muromonab-CD3 (Orthoclone®, "OK T3"), a murine IgG2a monoclonal antibody against CD3 receptor on T-cells, for example, can induce complement-induced lysis of CD3+ T-cells from the peripheral circulation and lymphoid tissues. Chatenoud, L. et al, Nat. Rev. Immunoo. 3, 123-32 (2003). However, the serious side effects associated with the immunogenic and mitogenic potential limits of OKT3 is wide spread with its use in treating TCL patients. For example, therapeutic benefits of OKT3 are hampered by the cytokine-based inflammatory response caused by the engagement of the antibody with the CD3 receptor. Abramowicz D, et al., Transplantation, 1989; 47:606-608. Moreover, the potent mitogenic properties of OKT3 for the T-cells may increase the proliferation of the malignant immune cells, thereby exacerbating the T-cell neoplasm in the TCL patients. Landergren U, et al., Eur J Immunol. 1984 April; 14(4):325-8.

Without being bound by theory, the binding agent is believed to be bound by the carrier protein through hydrophobic interactions, which, by their nature, are weak. Yet, the activity of the individual components, as well as their relative relationship in the nanoparticle, is preserved even upon lyophilization and reconstitution of the composition as hereinafter described. It is still further contemplated that binding to the carrier protein, e.g., complexation of the binding agent to the carrier protein, occurs through an albumin-binding motif on the binding agents and/or an antibody-binding motif on the carrier protein. In one embodiment, upon reconstitution with an aqueous solution, the antigen-binding portion of said binding agents is capable of binding to (recognizes) the antigen on a T-cell cancer. In another embodiment, fewer than about 50% of said nanoparticles are oligomeric.

Further challenges are imposed because the nanoparticles are used in therapy.

While rearrangement of the components in the nanoparticle may be mitigated through covalent bonds between the components, such covalent bonds pose challenges for the therapeutic use of nanoparticles in cancer treatment. The binding agent, carrier protein, and additional therapeutic agent typically act at different locations in a tumor and through different mechanisms. Non-covalent bonds permit the components of the nanoparticle to dissociate at the tumor. Thus, while a covalent bond may be advantageous for lyophilization, it may be disadvantageous for therapeutic use.

This disclosure is related to a nanoparticle composition that comprises nanoparticles having an outer surface, wherein each of the nanoparticles comprises: a carrier protein, a binding agent with an antigen-binding portion targeting an antigen expressed on a T cell, and optionally a therapeutically effective amount of a therapeutic agent.

The size of nanoparticles, and the distribution of the size, is also important. Nanoparticles may behave differently according to their size. At large sizes, nanoparticles or the agglomeration of the particles may block blood vessels, either of which can affect the performance and safety of the composition. In one embodiment, the average size of the nanoparticles is between 90 nm and 800 nm. In another embodiment, the average size of the nanoparticles is between 300 nm and 500 nm. In yet a further embodiment, the average size of the nanoparticles is about 90 nm to about 160 nm.

Finally, cryoprotectants and agents that assist in the lyophilization process must be safe and tolerated for therapeutic use.

In one aspect, the binding agent is capable of binding to an antigen expressed on T-cells or T-cell cancers in vivo. In another embodiment, the antigen-binding portion of the binding agent binds to an antigen expressed on a T-cell or a T-cell cancer. In one embodiment, the antigen is a protein expressed on the T-cell cancers, including but not limited to, CD2, CD3, CD4, CD5, CD8, CD25, CD30, CD40, CD52, CD 122, and CCR4. In a further embodiment, the antigen is a biomarker overexpressed in the T-cell cancers (e.g., T-cell lymphomas). The biomarkers may include PD-L1, Ly6E, HER3/EGFR DAF, ERBB-3 receptor, CSF-1R, HER2, STEAP1, CEA, OX40, Ang2-VEGF, or VEGF. In a preferred embodiment, the binding portion of the binding agent is capable of binding to CD2, CD3, CD4, CD5, CD8, CD25, CD30, CD40, CD52, CD 122, or CCR4. In another embodiment, the binding portion of the binding agent is capable of binding to PD-L1, Ly6E, HER3/EGFR DAF, ERBB-3 receptor, CSF-1R, HER2, STEAP1, CEA, OX40, Ang2-VEGF, or VEGF. In one embodiment, the T-cell cancer is T-cell lymphoma. In another embodiment, the T-cell cancer is peripheral T-cell lymphoma, anaplastic large cell lymphoma, angioimmunoblastic lymphoma cutaneous T-cell lymphoma, Adult T-cell Leukemia/Lymphoma (ATLL), enteropathy-type T-cell lymphoma, hematosplenic gamma-delta T-cell lymphoma, lymphoblastic lymphoma, nasal NK/T-cell lymphoma, treatment-related T-cell lymphoma, or a combination thereof. In one aspect, the antigen may exclude one or more of the antigens recited herein. In one embodiment, the antigen is not VEGF, HER2, or EGFR.

In one aspect, provided herein are nanoparticle compositions comprising nanoparticles wherein each of the nanoparticles comprises a carrier protein, binding agents with a T-cell antigen-binding portion, and optionally at least one therapeutic agent, wherein upon reconstitution with an aqueous solution, the antigen-binding portion of said binding agents are capable of binding to an antigen expressed on a T-cell in vivo.

When administered intravenously, large particles (e.g. greater than 1 μm) are typically disfavored because they can become lodged in the microvasculature of the lungs. At the same time, larger particles can accumulate in the tumor or specific organs. For example, THERASPHERE® 20-60 micron glass particles that are injected into the hepatic artery feeding a tumor of the liver for the delivery of a radioactive element, also known as radioembolization, are in clinical use for liver cancer.

Therefore, for intravenous administration, particles under 1 μm are used. Particles over 1 μm are, more typically, administered directly into a tumor ("direct injection") or into an artery feeding into the site of the tumor.

In one aspect, the nanoparticle comprises about 100 to about 1000 binding agents, preferably about 400 to about 800 binding agents. The number of binding agents in the composition also depends on the number of particles. When nanoparticles multimerize, the number of binding agents increases proportionally. For example, if a 160 nm nanoparticle contains 400 binding agents, a 320 nm dimer is expected to contain about 800 binding agents.

In other embodiments, the nanoparticles multimerize or oligomerize, e.g. dimerize. Multimerization may be observed as multiples of the weight or size of the unit molecule, e.g. 160 nm particles multimerize to about 320 nm, 480 nm, 640 nm, etc. In some embodiments, less than 40% of the nanoparticles in a population are oligomerized. In some embodiments, less than 30% of the nanoparticles are oligomerized. In a further embodiment, less than 20% of the nanoparticles are oligomerized. In another embodiment, less than 10% of the nanoparticles present are oligomerized. In a preferable embodiment, less than 5% of the nanoparticles are oligomerized.

In one embodiment, the weight ratio of carrier-bound drug to binding agent (e.g. albumin-bound paclitaxel to OKT3) is between about 5:1 to about 1:1. In one embodiment, the weight ratio of carrier-bound drug to binding agent is about 10:4. In one embodiment, the binding agents are a substantially single layer on all or part of the surface of the nanoparticle. In one embodiment, less than 0.01% of nanoparticles in the composition have a size selected from the group consisting of greater than 200 nm, greater than 300 nm, greater than 400 nm, greater than 500 nm, greater than 600 nm, greater than 700 nm and greater than 800 nm. Larger sizes are believed to be the result of multimerization (or oligomerization) of several nanoparticles.

The invention further includes lyophilized compositions, and lyophilized compositions that do not materially differ from, or are the same as, the properties of freshly-prepared nanoparticles. In particular, the lyophilized composition, upon resuspending in aqueous solution, is similar or identical to the fresh composition in terms of particle size, particle size distribution, toxicity for cancer cells, binding agent affinity, and binding agent specificity. Surprisingly, lyophilized nanoparticles retain the properties of freshly-made nanoparticles after resuspension notwithstanding the presence of two different protein components in these particles.

In one embodiment, the average reconstituted nanoparticle size is from about 90 nm to about 1 μm. In a preferred embodiment, the average reconstituted nanoparticle size is from about 90 nm to about 200 nm, and more preferably about 100 to about 160 nm. In one embodiment, in the average reconstituted nanoparticle size is from greater than 800 nm to about 3.5 μm, comprising multimers of smaller nanoparticles, e.g. multimers of 100-200 nm nanoparticles. In one embodiment, the weight ratio of core to binding agent is from greater than 1:1 to about 1:3. In one embodiment, in the average reconstituted nanoparticle size is about 160 nm to about 225 nm.

In one aspect, this invention relates to a lyophilized nanoparticle composition comprising nanoparticles, wherein each of the nanoparticles comprises a carrier-bound drug core and a binding agent. In one embodiment, the binding agents retain their association with the outside surface of the nanoparticle upon reconstitution with an aqueous solution. In one embodiment, after reconstitution, the binding agent is arranged on a surface of the core such that the binding portion of the binding agent is directed outward from that surface. In one embodiment, the lyophilized composition is stable at room temperature for at least about 3 months, 4 months, 5 months, 6 months, 7 months, 8 months, 9 months, 10 months, 11 months, 12 months, or longer. In one embodiment, the lyophilized composition is stable at room temperature for at least 3 months. In one embodiment, the reconstituted nanoparticles retain the activity of the therapeutic agent and are capable of binding to the target in vivo. In another embodiment, the composition is stable at about 20° C. to about 25° C. for up to about 12 months or longer.

In some embodiments, the at least one therapeutic agent is located inside the nanoparticle. In other embodiments, the at least one therapeutic agent is located on the outside surface of the nanoparticle. In yet other embodiments, the at least one therapeutic agent is located inside the nanoparticle and on the outside surface of the nanoparticle. In a further embodiment, the therapeutic agent is a therapeutic agent for cancer.

In some embodiments, the nanoparticle contains more than one type of therapeutic agent. In one embodiment, the therapeutic agent may be abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitiilnib, teniposide, triplatin, vinblastine, vinorelbine, vincristine, or cyclophosphamide. In a preferred embodiment, the therapeutic agent is Paclitaxel.

In another aspect, the binding agent comprises Slipizumab, OKT3, Leu 1, Zanolimumab, Brentuximab vedotin, Mik-β1, KW-0761, or a combination thereof. In some embodiments, the binding agent is muromonab-CD3 (OKT3).

In yet another embodiment, the antigen binding portion comprises an aptamer, a receptor ligand, an Fab fragment, or a combination thereof. In a preferred embodiment, the antigen binding portion is an antibody of portion thereof.

In some embodiments, the carrier protein comprises gelatin, elastin, gliadin, legumin, zein, a soy protein, a milk protein, and a whey protein. In other embodiments, the carrier protein is albumin, for example, human serum albumin. In some embodiments, the albumin is human serum albumin (HSA). In some embodiments, the albumin is a recombinant albumin, e.g., recombinant human serum albumin.

In some embodiments, the composition is formulated for intravenous delivery.

In some embodiments, the nanoparticles have a dissociation constant between about $1 \times 10^{-11}$M and about $1 \times 10^{-9}$M.

Also provided herein are methods for killing cancer cells in a T cell cancer, which comprise contacting the cell with an effective amount of a nanoparticle composition disclosed herein for a sufficient period of time to kill the cancerous T cells. In other embodiments, the nanoparticle composition is administered intravenously.

In some embodiments, the methods provided herein include the steps of: a) administering the nanoparticle composition once a week for three weeks; b) ceasing administration of the nanoparticle composition for one week; and c) repeating steps a) and b) as necessary to treat the tumor.

In related embodiments, the treatment comprises administration of the targeting binding agent prior to administration of the nanoparticles. In one embodiment, the targeting binding agent is administered between about 6 and 48, or 12 and 48 hours prior to administration of the nanoparticles. In another embodiment, the targeting binding agent is administered between 6 and 12 hours prior to administration of the nanoparticles. In yet another embodiment, the targeting binding agent is administered between 2 and 8 hours prior to administration of the nanoparticles. In still other embodiments, the targeting binding agent is administered a week prior to administration of the nanoparticles. For example, administration of a dose of OKT3 24 hours prior to administration of nanoparticles. In another example, OKT3 is administered prior to administering the nanoparticles. The binding agent administered prior to the nanoparticle may be administered as a dose that is subtherapeutic, such as ½, ¹/₁₀th or ¹/₂₀ the amount normally considered therapeutic. Thus, in humans, pretreatment with OKT3 may comprise administration of 1 mg/kg OKT3 which is ¹/₁₀th the usual dose, followed by administration of nanoparticles.

In some embodiments, the therapeutically effective amount comprises about 75 mg/m² to about 175 mg/m² of the carrier protein (i.e., milligrams carrier protein per m² of the patient). In other embodiments, the therapeutically effective amount comprises about 75 mg/m² to about 175 mg/m² of therapeutic agent (e.g., paclitaxel). In other embodiments, the therapeutically effective amount comprises about 30 mg/m² to about 70 mg/m² of the binding agent. In yet other embodiments, the therapeutically effective amount comprises about 30 mg/m² to about 70 mg/m² OKT3.

In one specific embodiment, the lyophilized composition comprises from about 75 mg/m² to about 175 mg/m² of the carrier protein which is preferably albumin; from about 30 mg/m² to about 70 mg/m² of the binding agent which is preferably OKT3; and from about 75 mg/m² to about 175 mg/m² of paclitaxel.

An embodiment of the invention includes a method for increasing the duration of cancer cell uptake of a chemotherapeutic agent by administering the chemotherapeutic agent in a nanoparticle comprising a carrier protein and the chemotherapeutic agent having surface complexation with an antibody, e.g., an antibody that specifically binds to an antigen on or shed by the cancer cell, wherein the cancer cell is a T cell.

Further provided herein are methods of making nanoparticle compositions, wherein said methods comprise contacting the carrier protein and the optionally at least one therapeutic agent with the antibodies in a solution having a pH of between 5.0 and 7.5 and a temperature between about 5° C. and about 60° C., between about 23° C. and about 60° C., or between about 55° C. and about 60° C. under conditions and ratios of components that will allow for formation of the desired nanoparticles. In one embodiment, the nanoparticle is made at 55° C. to 60° C. and pH 7.0. In another aspect, provided herein are methods of making the nanoparticle compositions, wherein said method comprises (a) contacting the carrier protein and optionally the at least one therapeutic agent to form a core and (b) contacting the core with the antibodies in a solution having a pH of about 5.0 to about 7.5 at a temperature between about 5° C. and about 60° C., between about 23° C. and about 60° C., or between about 55° C. and about 60° C. under conditions and ratios of components that will allow for formation of the desired nanoparticles.

The amount of components (e.g., carrier protein, antibodies, therapeutic agents, combinations thereof) is controlled in order to provide for formation of the desired nanoparticles. A composition wherein the amount of components is too dilute will not form the nanoparticles as described herein. In a preferred embodiment, weight ratio of carrier protein to binding agent is 10:4. In some embodiments, the amount of carrier protein is between about 1 mg/mL and about 100 mg/mL. In some embodiments, the amount of binding agent is between about 1 mg/mL and about 30 mg/mL. For example, in some embodiments, the ratio of carrier protein:binding agent:solution is approximately 9 mg of carrier protein (e.g., albumin) to 4 mg of binding agent (e.g., OKT3) in 1 mL of solution (e.g., saline). An amount of a therapeutic agent, such as, for example, paclitaxel, can also be added to the carrier protein, for example prior to contacting the antibody.

BRIEF DESCRIPTION OF THE DRAWINGS

The following figures are representative only of the invention and are not intended as a limitation. For the sake of consistency, the nanoparticles of this invention using ABRAXANE® and bevacizumab employ the acronym "AB" and the number after AB such as AB160 is meant to confer the average particle size of these nanoparticles (in nanometers). Likewise, when the binding agent is rituximab, the acronym is "AR" while the number thereafter remains the same.

FIG. 1 shows the binding affinity of Abraxane and OKT3 as determined by light absorption Bio-layer interferometry (BLItz) technology. The dissociation constant (Kd) is $2.246 \times 10^{-9}$.

DETAILED DESCRIPTION

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between.

Preferably, the term "about" when used with regard to a dose amount means that the dose may vary by +/−10%. For example, "about 400 to about 800 binding agents" indicates that an outside surface of a nanoparticles contain an amount of binding agent between 360 and 880 particles.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "nanoparticle" as used herein refers to particles having at least one dimension which is less than 5 microns. In preferred embodiments, such as for intravenous administration, the nanoparticle is less than 1 micron. For direct administration, the nanoparticle is larger. Even larger particles are expressly contemplated by the invention.

In a population of particles, the sizes of individual particles are distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50.

The term "nanoparticle" may also encompass discrete multimers of smaller unit nanoparticles. For example, a 320 nm particle may comprise a dimer of a unit 160 nm nanoparticle. For 160 nm nanoparticles, multimers would therefore be approximately 320 nm, 480 nm, 640 nm, 800 nm, 960 nm, 1120 nm, and so on.

The term "carrier protein" as used herein refers to proteins that function to transport binding agents and/or therapeutic agents. The binding agents of the present disclosure can reversibly bind to the carrier proteins. Examples of carrier proteins are discussed in more detail below.

The term "core" as used herein refers to central or inner portion of the nanoparticle which may be comprised of a carrier protein, a carrier protein and a therapeutic agent, or other agents or combination of agents. In some embodiments, a hydrophobic portion of the binding agent may be incorporated into the core.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof.

As used herein, the term "binding agent", "binding agent specific for", or "binding agent that specifically binds" refers to an agent that binds to a target antigen and does not significantly bind to unrelated compounds. Examples of binding agents that can be effectively employed in the disclosed methods include, but are not limited to, lectins, proteins, and antibodies, such as monoclonal antibodies, e.g. humanized monoclonal antibodies, chimeric antibodies, or polyclonal antibodies, or antigen-binding fragments thereof, as well as aptamers or fusion proteins. In one embodiment, the binding agent comprises an albumin-binding motif. Non-limiting examples of albumin-binding motifs can be found in PCT Application No. PCT/US2017/045643, filed Aug. 4, 2017, which is incorporated herein by reference in its entirety. In an embodiment, the binding agent is an exogenous antibody. An exogenous antibody is an antibody not naturally produced in a mammal, e.g. in a human, by the mammalian immune system.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., *Eur. J Immunol.* 17, 105 (1987)) and single chains (e.g., Huston et al., *Proc. Natl. Acad. Sci. U.S.A.*, 85, 5879-5883 (1988) and Bird et al., *Science* 242, 423-426 (1988), which are incorporated herein by reference). (See, generally, Hood et al., *Immunology*, Benjamin, N.Y., 2ND ed. (1984); Harlow and Lane, *Antibodies. A Laboratory Manual*, Cold Spring Harbor Laboratory (1988); Hunkapiller and Hood, *Nature*, 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. Antibody or antibodies include any biosimilar(s) of the antibodies disclosed herein. Biosimilars, as used herein, refers to a biopharmaceutical which is deemed to be comparable in quality, safety, and efficacy to a reference product marketed by an innovator company (Section 351(i) of the Public Health Service Act (42 U.S.C. 262(i)).

The term "dissociation constant," also referred to as "$K_d$," refers to a quantity expressing the extent to which a particular substance separates into individual components (e.g., the protein carrier, antibody, and therapeutic agent).

The terms "lyophilized," "lyophilization" and the like as used herein refer to a process by which the material (e.g., nanoparticles) to be dried is first frozen and then the ice or frozen solvent is removed by sublimation in a vacuum environment. An excipient is optionally included in pre-lyophilized formulations to enhance stability of the lyophilized product upon storage. In some embodiments, the nanoparticles can be formed from lyophilized components (carrier protein, antibody and optional therapeutic) prior to use as a therapeutic. In other embodiments, the carrier protein, binding agent, e.g., antibody, and optional therapeutic agent are first combined into nanoparticles and then lyophilized. The lyophilized sample may further contain additional excipients.

The term "bulking agents" comprise agents that provide the structure of the freeze-dried product. Common examples used for bulking agents include mannitol, glycine, lactose and sucrose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers. In some embodiments, the lyophilized compositions comprise a bulking agent. In some embodiments, the lyophilized compositions do not comprise a bulking agent.

The term "buffer" encompasses those agents which maintain the solution pH in an acceptable range prior to lyophilization and may include succinate (sodium or potassium), histidine, phosphate (sodium or potassium), Tris(tris (hydroxymethyl)aminomethane), diethanolamine, citrate (sodium) and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "cryoprotectants" generally includes agents which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as sucrose, glucose, trehalose, and lactose; surfactants such as polysorbates; and amino acids such as glycine, arginine, and serine.

The term "lyoprotectant" includes agents that provide stability to the protein during the drying or 'dehydration' process (primary and secondary drying cycles), presumably by providing an amorphous glassy matrix and by binding with the protein through hydrogen bonding, replacing the water molecules that are removed during the drying process. This helps to maintain the protein conformation, minimize protein degradation during the lyophilization cycle and improve the long-term products. Examples include polyols or sugars such as sucrose and trehalose.

The term "pharmaceutical formulation" refers to preparations which are in such form as to permit the active ingredients to be effective, and which contains no additional components that are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation into a solution.

A "stable" formulation is one in which the protein therein essentially retains its physical stability and/or chemical stability and/or biological activity upon storage. For example, various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. *Adv. Drug Delivery Rev.* 10:29-90 (1993). Stability can be measured at a selected temperature for a selected time period.

The term "epitope" as used herein refers to the portion of an antigen which is recognized by a binding agent, e.g., an antibody. Epitopes include, but are not limited to, a short amino acid sequence or peptide (optionally glycosylated or otherwise modified) enabling a specific interaction with a protein (e.g., an antibody) or ligand. For example, an epitope may be a part of a molecule to which the antigen-binding site of a binding agent attaches.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. In some embodiments "treating" or "treatment" refers to the killing of cancer cells.

The term "kill" or "killing" with respect to a cancer treatment is directed to include any type of manipulation that will lead to the death of that cancer cell or at least of portion of a population of cancer cells.

The term "aptamer" refers to a nucleic acid molecule that is capable of binding to a target molecule, such as a polypeptide. For example, an aptamer of the invention can specifically bind to the antigen expressed on a T-cell cancer, e.g., CD2, CD3, CD4, CD5, CD8, CD20, CD38, CD25, CD30, CD40, CD52, CD 122, or CCR4. The generation of antibodies with a particular binding specificity and the therapeutic use of aptamers are well established in the art. See, e.g., U.S. Pat. Nos. 5,475,096, 5,270,163, 5,582,981, 5,840,867, 6,011,020, 6,051,698, 6,147,204, 6,180,348 and 6,699,843, and the therapeutic efficacy of Macugen® (Eyetech, New York) for treating age-related macular degeneration.

The term "oligomer" or "oligomeric" or "oligomerized" as used herein refers to oligomers composed of two or more monomers.

Fusion proteins are bioengineered polypeptides that join one portion of a protein (e.g., the crystallizable fragment (Fc) domain of an antibody; or an albumin-binding motif of an antibody) with another biologically active agent, e.g., a protein domain, peptide, or nucleic acid or peptide aptamer, to generate a molecule with desired structure-function properties and significant therapeutic potential. The gamma immunoglobulin (IgG) isotype is often used as the basis for generating Fc-fusion proteins because of favorable characteristics such as recruitment of effector function and increased plasma half-life. Given the range of aptamers, both peptide and nucleic acids, that can be used as fusion partners, fusion proteins have numerous biological and pharmaceutical applications.

Additionally, some terms used in this specification are more specifically defined below.

Overview

The current invention is predicated, in part, on the surprising discovery that optionally lyophilized nanoparticles comprising a carrier protein, a binding agent, e.g., an antibody, an aptamer, or a fusion protein having an albumin-binding motif and an antigen binding domain, e.g., an albumin-binding motif fused to an aptamer or the ligand of a cellular receptor, capable of binding to an antigen expressed on a T-cell or a T-cell cancer, and a therapeutic agent provide targeted therapy to a tumor while minimizing toxicity to the patient. In one aspect, the binding agent is OKT3 capable of binding to an antigen expressed on a T-cell or a T-cell cancer while, at the same time, reducing or elimination the serious side effects associated with the immunogenic and mitogenic potential limits of OKT3. Accordingly, the nanoparticles as described herein are thus a significant improvement compared to the conventional ADCs having serious side effects and/or toxicity.

As would be understood by one skilled in the art, for conventional ADCs to be effective, it is critical that the linker be stable enough not to dissociate in the systemic circulation but allow for sufficient drug release at the tumor site. Alley, S. C., et al. (2008) *Bioconjug Chem* 19:759-765. This has proven to be a major hurdle in developing effective drug conjugate (Julien, D. C., et al. (2011) MAbs 3:467-478; Alley, S. C., et al. (2008) *Bioconjug Chem* 19:759-765); therefore, an attractive feature of the nano-immune conjugate is that a biochemical linker is not required.

Another shortcoming of current ADCs is that higher drug penetration into the tumor has not been substantively proven in human tumors. Early testing of ADCs in mouse models suggested that tumor targeting with antibodies would result in a higher concentration of the active agent in the tumor (Deguchi, T. et al. (1986) *Cancer Res* 46: 3751-3755); however, this has not correlated in the treatment of human disease, likely because human tumors are much more heterogeneous in permeability than mouse tumors. Jain, R. K. et al. (2010) *Nat Rev Clin Oncol* 7:653-664. Also, the size of the nanoparticle is critical for extravasation from the vasculature into the tumor. In a mouse study using a human colon adenocarcinoma xenotransplant model, the vascular pores were permeable to liposomes up to 400 nm. Yuan, F., et al. (1995) *Cancer Res* 55: 3752-3756. Another study of tumor pore size and permeability demonstrated that both characteristics were dependent on tumor location and growth status, with regressing tumors and cranial tumors permeable to particles less than 200 nm. Hobbs, S. K., et al. (1998) *Proc Natl Acad Sci USA* 95:4607-4612. The nano-immune conjugate described herein overcomes this issue by the fact that the large complex, which is less than 200 nm intact, is partially dissociated in systemic circulation into smaller functional units that are easily able to permeate tumor tissue. Furthermore, once the conjugate arrives to the tumor site, the smaller toxic payload can be released and only the toxic portion needs to be taken up by tumor cells, not the entire conjugate.

The advent of antibody- (i.e. AVASTIN®) coated albumin nanoparticles containing a therapeutic agent (i.e., ABRAXANE®) has led to a new paradigm of directional delivery of two or more therapeutic agents to a predetermined site in vivo. See PCT Patent Publication Nos. WO 2012/154861 and WO 2014/055415, each of which is incorporated herein by reference in its entirety.

When compositions of albumin and an binding agent, e.g., antibody, are admixed together in an aqueous solution at specific concentrations and ratios, the binding agents useful in this invention spontaneously self-assemble into and onto the albumin to form nanoparticles having multiple copies of the binding agent (up to 500 or more).

While protein compositions comprising a single source protein are commonly stored in lyophilized form where they exhibit significant shelf-life, such lyophilized compositions do not contain a self-assembled nanoparticle of two different proteins integrated together by hydrophobic-hydrophobic interactions. Moreover, the nanoparticle configuration wherein a majority of the binding portions of the binding agent are exposed on the surface of the nanoparticles lends itself to being susceptible to dislodgement or reconfiguration by conditions which otherwise would be considered benign. For example, during lyophilization, ionic charges on the proteins are dehydrated thereby exposing the underlying charges. Exposed charges allow for charge-charge interactions between the two proteins which can alter the binding affinity of each protein to the other. In addition, the concentration of the nanoparticles increases significantly as the solvent (e.g., water) is removed. Such increased concentrations of nanoparticles could lead to irreversible oligomerization. Oligomerization is a known property of proteins that reduces the biological properties of the oligomer as compared to the monomeric form and increases the size of the particle sometimes beyond 1 micron.

On the other hand, a stable form of a nanoparticle composition is required for clinical and/or commercial use where a shelf-life of at least 3 months is required and shelf-lives of greater than 6 months or 9 months are preferred. Such a stable composition must be readily available for intravenous injection, must retain its self-assembled form upon intravenous injection so as to direct the nanoparticle to the predetermined site in vivo, must have a maximum size of less than 1 micron so as to avoid any ischemic event when delivered into the blood stream, and finally must be compatible with the aqueous composition used for injection.

Compounds

As will be apparent to the skilled artisan upon reading this disclosure, the present disclosure relates to compositions of nanoparticles containing a carrier protein, binding agents, and at least one therapeutic agent, wherein said compositions are optionally lyophilized.

In some embodiments, the carrier protein can be albumin, gelatin, elastin (including topoelastin) or elastin-derived polypeptides (e.g., α-elastin and elastin-like polypeptides (ELPs)), gliadin, legumin, zein, soy protein (e.g., soy protein isolate (SPI)), milk protein (e.g., β-lactoglobulin (BLG) and casein), or whey protein (e.g., whey protein concentrates (WPC) and whey protein isolates (WPI)). In preferred embodiments, the carrier protein is albumin. In preferred embodiments, the albumin is egg white (ovalbumin), bovine serum albumin (BSA), or the like. In even more preferred embodiments, the carrier protein is human serum albumin (HSA). In some embodiments, the carrier protein (e.g., albumin) is a recombinant protein (e.g., recombinant HSA). In some embodiments, the carrier protein is a generally regarded as safe (GRAS) excipient approved by the United States Food and Drug Administration (FDA). In one embodiment, the carrier protein comprises an antibody-binding motif. Non-limiting examples of antibody-binding motifs can be found in PCT Application No. PCT/US2017/045643, filed Aug. 4, 2017, which is incorporated herein by reference in its entirety.

In some embodiments, the binding agents are antibodies selected from the group consisting of ado-trastuzumab emtansine, alemtuzumab, bevacizumab, cetuximab, denosumab, dinutuximab, ipilimumab, nivolumab, obinutuzumab, ofatumumab, panitumumab, pembrolizumab, pertuzumab, rituximab, and trastuzumab. In some embodiment, the binding agents are antibodies comprising Slipizumab, OKT3, Leu 1, Zanolimumab, Zanolimumab, Brentuximab vedotin, Mik-β1, KW-0761, or a combination thereof. In some embodiments, one or more of these antibodies are explicitly excluded. In some embodiments, the antibodies are a substantially single layer of antibodies on all or part of the surface of the nanoparticle.

In one aspect, the binding portion of the antibody is capable of binding to an antigen expressed on a T-cell or a T-cell cancer. In one embodiment, the antigen is a protein expressed on the T-cell cancers, including but not limited to, CD2, CD3, CD4, CD5, CD8, CD25, CD30, CD40, CD52, CD 122, and CCR4. In a further embodiment, the antigen is a biomarker overexpressed in the T-cell cancers (e.g., T-cell lymphomas). The biomarkers overexpressed in the T-cell cancers may include PD-L1, Ly6E, HER3/EGFR DAF, ERBB-3 receptor, CSF-1R, HER2, STEAP1, CEA, OX40, Ang2-VEGF, or VEGF. In a preferred embodiment, the binding portion of the antibody is capable of binds CD2, CD3, CD4, CD5, CD8, CD25, CD30, CD40, CD52, CD 122, or CCR4. In another embodiment, the binding portion of the antibody is capable of binding PD-L1, Ly6E, HER3/EGFR DAF, ERBB-3 receptor, CSF-1R, HER2, STEAP1, CEA, OX40, Ang2-VEGF, or VEGF.

Table 1 depicts a list of non-limiting list of monoclonal antibodies for treating T-cell leukemia and lymphoma.

TABLE 1

Monoclonal antibodies for treating T-cell cancers.

| Target Antigen | Description | Monoclonal Antibody |
|---|---|---|
| CD2 | LFA-3 (CD58) | Slipizumab (MEDI-507) |
| CD3 (CD3ζ) | TcR signaling chain | muromonab-CD3 (Orthoclone ®, OKT3) |
| CD4 | TcR co-receptor | Zanolimumab (HuMax-CD4 ®) |
| CD5 | Scavenger receptor family member | Anti-Leu1/T101 |
| CD25 | IL-2 receptor α-subunit | Daclizumab (Zenapax ®) |
| CD30 | TNF receptor family member | Brentuximab vedotin (Adcetris ®) |
| CD52 | GPI-anchored glycoprotein | Alemtuzumab (Campath ®) |
| CD122 | β-subunit of the IL-2 and IL-15 receptor | Mik-β1 |
| CCR4 | Chemokine receptor-4 | KW-0761 |

In some embodiments, the at least one therapeutic agent, or the at least one additional therapeutic agent, is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide. In one embodiment, the therapeutic agent comprises one or more of Adriamycin, bleomycin, vinblastine sulfate, vincristine sulfate, etoposide, prednisone, cyclophosphamide and dacarbazine. In one embodiment, the therapeutic agent comprises one or more of arranon (Nelarabine), abitrexate, adriamycin (doxorubicin hydrochloride), ambochlorin (Chlorambucil), Zydelig (Idelalisib), Vincasar PFS (Vincristine Sulfate), Velsar (Vinblastine Sulfate), Velcade (Bortezomib), Velban (Vinblastine Sulfate), Treanda (Bendamustine Hydrochloride), Romidepsin, Rheumatrex (Methotrexate), Revlimid (Lenalidomide), Procarbazine Hydrochloride, Prednisone, Pralatrexate, Plerixafor, Neosar (Cyclophosphamide), Mustargen (Mechlorethamine Hydrochloride), Methotrexate, Mechlorethamine Hydrochloride, Matulane (Procarbazine Hydrochloride), Lomustine, Linfolizin or Leukeran (Chlorambucil), Istodax (Romidepsin), Imbruvica (Ibrutinib), DTIC-Dome (Dacarbazine), Doxorubicin Hydrochloride, Denileukin Diftitox, Cytoxan (Cyclophosphamide), Carmustine, Beleodaq (Belinostat), or Arranon (Nelarabine). In one embodiment, the therapeutic agent comprises one or more of a mustard derivative (e.g., Cyclophosphamide, Mechlorethamine or Ifosfamide), Doxorubicin, Vinblastine, Vincristine, Bleomycin, Etoposide, and Prednisone. One of skill in the art would understand that these are merely examples, and any chemotherapeutic agent or cancer therapeutic agent may be included.

Preferably, the nanoparticles comprise paclitaxel as a therapeutic agent.

It is to be understood that the therapeutic agent may be located inside the nanoparticle, on the outside surface of the nanoparticle, or both. The nanoparticle may contain more than one therapeutic agent, for example, two therapeutic agents, three therapeutic agents, four therapeutic agents, five therapeutic agents, or more. Furthermore, a nanoparticle may contain the same or different therapeutic agents inside and outside the nanoparticle.

In one aspect, the nanoparticle comprises at least 100 binding agents non-covalently bound to the surface of the nanoparticle. In one aspect, the nanoparticle comprises at least 200 binding agents non-covalently bound to the surface of the nanoparticle. In one aspect, the nanoparticle comprises at least 300 binding agents non-covalently bound to the surface of the nanoparticle. In one aspect, the nanoparticle comprises at least 400 binding agents non-covalently bound to the surface of the nanoparticle. In one aspect, the nanoparticle comprises at least 500 binding agents non-covalently bound to the surface of the nanoparticle. In one aspect, the nanoparticle comprises at least 600 binding agents non-covalently bound to the surface of the nanoparticle.

In one aspect, the nanoparticle comprises between about 100 and about 1000 binding agents non-covalently bound to the surface of the nanoparticle. In one aspect, the nanoparticle comprises between about 200 and about 1000 binding agents non-covalently bound to the surface of the nanoparticle. In one aspect, the nanoparticle comprises between about 300 and about 1000 binding agents non-covalently bound to the surface of the nanoparticle. In one aspect, the nanoparticle comprises between about 400 and about 1000 binding agents non-covalently bound to the surface of the nanoparticle. In one aspect, the nanoparticle comprises between about 500 and about 1000 binding agents non-covalently bound to the surface of the nanoparticle. In one aspect, the nanoparticle comprises between about 600 and about 1000 binding agents non-covalently bound to the surface of the nanoparticle. In one aspect, the nanoparticle comprises between about 200 and about 800 binding agents non-covalently bound to the surface of the nanoparticle. In one aspect, the nanoparticle comprises between about 300 and about 800 binding agents non-covalently bound to the surface of the nanoparticle. In preferred embodiments, the nanoparticle comprises between about 400 and about 800 binding agents non-covalently bound to the surface of the nanoparticle. Contemplated values include any value or subrange within any of the recited ranges, including endpoints.

In one aspect, the average particle size in the nanoparticle composition is less than about 1 μm. In one aspect, the average particle size in the nanoparticle composition is between about 90 nm and about 1 μm. In one aspect, the average particle size in the nanoparticle composition is between about 90 nm and about 900 nm. In one aspect, the average particle size in the nanoparticle composition is between about 90 nm and about 800 nm. In one aspect, the average particle size in the nanoparticle composition is between about 90 nm and about 700 nm. In one aspect, the average particle size in the nanoparticle composition is between about 90 nm and about 600 nm. In one aspect, the average particle size in the nanoparticle composition is between about 90 nm and about 500 nm. In one aspect, the average particle size in the nanoparticle composition is between about 90 nm and about 400 nm. In one aspect, the average particle size in the nanoparticle composition is between about 90 nm and about 300 nm. In one aspect, the average particle size in the nanoparticle composition is between about 90 nm and about 200 nm. In a preferred embodiment, the average particle size in the nanoparticle composition is between about 100 nm and about 180 nm. In an especially preferred embodiment, the mean particle size in the nanoparticle composition is about 100 nm to about 160 nm. Contemplated values include any value, subrange, or range within any of the recited ranges, including endpoints.

In one aspect, the nanoparticle composition is formulated for intravenous injection. In order to avoid an ischemic event, the nanoparticle composition formulated for intravenous injection should comprise nanoparticles with an average particle size of less than about 1 μm.

In one aspect, the average particle size in the nanoparticle composition is greater than about 1 μm. In one aspect, the average particle size in the nanoparticle composition is between about 1 μm and about 5 μm. In one aspect, the average particle size in the nanoparticle composition is between about 1 μm and about 4 μm. In one aspect, the average particle size in the nanoparticle composition is between about 1 μm and about 3 μm. In one aspect, the average particle size in the nanoparticle composition is between about 1 μm and about 2 μm. In one aspect, the average particle size in the nanoparticle composition is between about 1 μm and about 1.5 μm. Contemplated values include any value, subrange, or range within any of the recited ranges, including endpoints.

In one aspect, the nanoparticle composition is formulated for direct injection into a tumor. Direct injection includes injection into or proximal to a tumor site, perfusion into a tumor, and the like. When formulated for direct injection into a tumor, the nanoparticle may comprise any average particle size. Without being bound by theory, it is believed that larger particles (e.g., greater than 500 nm, greater than 1 μm, and the like) are more likely to be immobilized within the tumor, thereby providing a beneficial effect. Larger particles can accumulate in the tumor or specific organs. See, e.g., 20-60 micron glass particle that is used to inject into the hepatic artery feeding a tumor of the liver, called "TheraSphere®" (in clinical use for liver cancer). Therefore, for intravenous administration, particles under 1 μm are typically used. Particles over 1 μm are, more typically, administered directly into a tumor ("direct injection") or into an artery feeding into the site of the tumor.

In one aspect, less than about 0.01% of the nanoparticles within the composition have a particle size greater than 200 nm, greater than 300 nm, greater than 400 nm, greater than 500 nm, greater than 600 nm, greater than 700 nm, or greater than 800 nm. In one aspect, less than about 0.001% of the nanoparticles within the composition have a particle size greater than 200 nm, greater than 300 nm, greater than 400 nm, greater than 500 nm, greater than 600 nm, greater than 700 nm, or greater than 800 nm. In a preferred embodiment, less than about 0.01% of the nanoparticles within the composition have a particle size greater than 800 nm. In a more preferred embodiment, less than about 0.001% of the nanoparticles within the composition have a particle size greater than 800 nm.

In a preferred aspect, the sizes and size ranges recited herein relate to particle sizes of the reconstituted lyophilized nanoparticle composition. That is, after the lyophilized nanoparticles are resuspended in an aqueous solution (e.g., water, other pharmaceutically acceptable excipient, buffer, etc.), the particle size or average particle size is within the range recited herein.

In one aspect, at least about 50%, 60%, 70%, 80%, 90%, 95%, 96%, 97%, 98%, 99%, 99.5%, or 99.9% of the nanoparticles are present in the reconstituted composition as single nanoparticles. That is, fewer than about 50%, 40%, 30%, etc. of the nanoparticles are dimerized or multimerized (oligomerized).

In some embodiments, the nanoparticles in the composition have less than 20% by number dimerization, less than 10% by number dimerization and preferably less than 5% dimerization.

In some embodiments, the size of the nanoparticle can be controlled by the adjusting the amount (e.g., ratio) of carrier protein to binding agent. The size of the nanoparticles, and the size distribution, is also important. The nanoparticles of the invention may behave differently according to their size. At large sizes, an agglomeration may block blood vessels. Therefore, agglomeration of nanoparticles can affect the performance and safety of the composition. On the other hand, larger particles may be more therapeutic under certain conditions (e.g., when not administered intravenously).

In one aspect, the nanoparticle composition comprises at least one additional therapeutic agent. In one embodiment, the at least one additional therapeutic agent is non-covalently bound to the outside surface of the nanoparticle. In one embodiment, the at least one additional therapeutic agent is arranged on the outside surface of the nanoparticle. In one embodiment, the at least one additional therapeutic agent is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gemcitabine, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, and cyclophosphamide. In one embodiment, the at least one additional therapeutic agent is an anti-cancer binding agent, e.g., an anti-cancer antibody.

Methods of Making Nanoparticles

In some aspects, the current invention relates to methods of making nanoparticle compositions as described herein. Nanoparticles as described herein can be made by any method. Non-limiting examples of methods of making nanoparticles, nanoparticle compositions, and lyophilized nanoparticle compositions can be found in PCT Pub. Nos. WO2014/055415 and WO2016/057554, each of which is incorporated herein by reference in its entirety.

In one aspect, the nanoparticles of the nanoparticle composition are formed by contacting the carrier protein or carrier protein-therapeutic agent particle with the binding agent at a ratio of about 10:1 to about 10:30 carrier protein particle or carrier protein-therapeutic agent particle to binding agent. In one embodiment, the ratio is about 10:2 to about 10:25. In one embodiment, the ratio is about 10:2 to about 1:1. In a preferred embodiment, the ratio is about 10:2 to about 10:6. In an especially preferred embodiment, the ratio is about 10:4. Contemplated ratios include any value, subrange, or range within any of the recited ranges, including endpoints.

In one embodiment, the amount of solution or other liquid medium employed to form the nanoparticles is particularly important. No nanoparticles are formed in an overly dilute solution of the carrier protein (or carrier protein-therapeutic agent) and the antibodies. An overly concentrated solution will result in unstructured aggregates. In some embodiments, the amount of solution (e.g., sterile water, saline, phosphate buffered saline) employed is between about 0.5 mL of solution to about 20 mL of solution. In some embodiments, the amount of carrier protein is between about 1 mg/mL and about 100 mg/mL. In some embodiments, the amount of binding agent is between about 1 mg/mL and about 30 mg/mL. For example, in some embodiments, the ratio of carrier protein:binding agent:solution is approximately 9 mg of carrier protein (e.g., albumin) to 4 mg of binding agent, e.g., antibody (e.g., OKT3) in 1 mL of solution (e.g., saline). An amount of a therapeutic agent (e.g., Taxol) can also be added to the carrier protein. For example, 1 mg of Taxol can be added 9 mg of carrier protein (10 mg carrier protein-therapeutic) and 4 mg of binding agent, e.g., antibody, Fc fusion molecule, or aptamer, in 1 mL of solution. When using a typical i.v. bag, for example, with the solution of approximately 1 liter one would need to use 1000× the amount of carrier protein/carrier protein-therapeutic agent and antibodies compared to that used in 1 mL. Thus, one cannot form the present nanoparticles in a standard i.v. bag. Furthermore, when the components are added to a standard i.v. bag in the therapeutic amounts of the present invention, the components do not self-assemble to form nanoparticles.

In one embodiment, the carrier protein or carrier protein-therapeutic agent particle is contacted with the binding agent in a solution having a pH between about 4 and about 8.

In one embodiment, the carrier protein or carrier protein-therapeutic agent particle is contacted with the binding agent in a solution having a pH of about 4. In one embodiment, the carrier protein or carrier protein-therapeutic agent particle is contacted with the binding agent in a solution having a pH of about 5. In one embodiment, the carrier protein or carrier protein-therapeutic agent particle is contacted with the binding agent in a solution having a pH of about 6. In one embodiment, the carrier protein or carrier protein-therapeutic agent particle is contacted with the binding agent in a solution having a pH of about 7. In one embodiment, the carrier protein or carrier protein-therapeutic agent particle is contacted with the binding agent in a solution having a pH of about 8. In a preferred embodiment, the carrier protein or carrier protein-therapeutic agent particle is contacted with the binding agent in a solution having a pH between about 5 and about 7.

In one embodiment, the carrier protein particle or carrier protein-therapeutic agent particle is incubated with the binding agent at a temperature of about 5° C. to about 60° C., or any range, subrange, or value within that range including endpoints. In a preferred embodiment, the carrier protein particle or carrier protein-therapeutic agent particle is incubated with the binding agent at a temperature of about 23° C. to about 60° C.

Without being bound by theory, it is believed that the stability of the nanoparticles within the nanoparticle composition is, at least in part, dependent upon the temperature and/or pH at which the nanoparticles are formed, as well as the concentration of the components (i.e., carrier protein, binding agent, and optionally therapeutic agent) in the solution. In one embodiment, the $K_d$ of the nanoparticles is between about $1 \times 10^{-11}$ M and about $2 \times 10^{-5}$ M. In one embodiment, the $K_d$ of the nanoparticles is between about $1 \times 10^{-11}$ M and about $2 \times 10^{-8}$ M. In one embodiment, the $K_d$ of the nanoparticles is between about $1 \times 10^{-11}$ M and about $7 \times 10^{-9}$ M. In a preferred embodiment, the $K_d$ of the nanoparticles is between about $1 \times 10^{-11}$ M and about $3 \times 10^{-8}$ M. Contemplated values include any value, subrange, or range within any of the recited ranges, including endpoints.

Lyophilization

The lyophilized compositions of this invention are prepared by standard lyophilization techniques with or without the presence of stabilizers, buffers, etc. Surprisingly, these conditions do not alter the relatively fragile structure of the nanoparticles. Moreover, at best, these nanoparticles retain their size distribution upon lyophilization and, more importantly, can be reconstituted for in vivo administration (e.g., intravenous delivery) in substantially the same form and ratios as if freshly made.

Lyophilization, or freeze-drying, removes water from a composition. In the process, the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al., Pharm. Res. 8(3):285-291 (1991).

While proteins may be lyophilized, the process of lyophilization and reconstitution may affect the properties of the protein. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation. aggregation, precipitation or adsorption, for example. The three most common protein degradation pathways are protein aggregation, deamidation and oxidation. Cleland, et al., Critical Reviews in Therapeutic Drug Carrier Systems 10(4): 307-377 (1993).

Formulations

In one aspect, the nanoparticle composition is formulated for systemic delivery, e.g., intravenous administration.

In one aspect, the nanoparticle composition is formulated for direct injection into a tumor. Direct injection includes injection into or proximal to a tumor site, perfusion into a tumor, and the like. Because the nanoparticle composition is not administered systemically, a nanoparticle composition is formulated for direct injection into a tumor may comprise any average particle size. Without being bound by theory, it is believed that larger particles (e.g., greater than 500 nm, greater than 1 μm, and the like) are more likely to be immobilized within the tumor, thereby providing what is believed to be a better beneficial effect.

In another aspect, provided herein is a composition comprising a compound provided herein, and at least one pharmaceutically acceptable excipient.

In general, the compounds provided herein can be formulated for administration to a patient by any of the accepted modes of administration. Various formulations and drug delivery systems are available in the art. See, e.g., Gennaro, A. R., ed. (1995) *Remington's Pharmaceutical Sciences*, 18th ed., Mack Publishing Co.

In general, compounds provided herein will be administered as pharmaceutical compositions by any one of the following routes: oral, systemic (e.g., transdermal, intranasal or by suppository), or parenteral (e.g., intramuscular, intravenous or subcutaneous) administration.

The compositions are comprised of, in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Treatment Methods

The nanoparticle compositions as described herein are useful in treating cancer cells and/or tumors in a mammal. In a preferred embodiment, the mammal is a human (i.e., a human patient). Preferably, the lyophilized nanoparticle composition is reconstituted (suspended in an aqueous excipient) prior to administration.

In one aspect is provided a method for treating a cancer cell, the method comprising contacting the cell with an effective amount of nanoparticle composition as described herein to treat the cancer cell. Treatment of a cancer cell includes, without limitation, reduction in proliferation, killing the cell, preventing metastasis of the cell, and the like.

In one aspect is provided a method for treating T-cells or T-cell cancers in a patient in need thereof, the method comprising administering to the patient a therapeutically effective amount of a nanoparticle composition as described herein to treat the T-cell cancer, where the T-cell cancer is peripheral T-cell lymphoma, anaplastic large cell lymphoma, angioimmunoblastic lymphoma cutaneous T-cell lymphoma, Adult T-cell Leukemia/Lymphoma (ATLL), enteropathy-type T-cell lymphoma, hematosplenic gamma-delta T-cell lymphoma, blastic NK-cell lymphoma, lymphoblastic lymphoma, nasal NK/T-cell lymphoma, treatment-related T-cell lymphoma, or a combination thereof.

In one aspect is provided a method for treating a tumor in a patient in need thereof, the method comprising administering to the patient a therapeutically effective amount of a nanoparticle composition as described herein to treat the tumor. In one embodiment, the size of the tumor is reduced. In one embodiment, the tumor size does not increase (i.e. progress) for at least a period of time during and/or after treatment.

In one embodiment, the nanoparticle composition is administered intravenously. In one embodiment, the nanoparticle composition is administered directly to the tumor. In one embodiment, the nanoparticle composition is administered by direct injection or perfusion into the tumor.

In one embodiment, the method comprises: a) administering the nanoparticle composition once a week for three weeks; b) ceasing administration of the nanoparticle composition for one week; and c) optionally repeating steps a) and b) as necessary to treat the tumor.

In one embodiment, the therapeutically effective amount of the nanoparticles described herein comprises about 1 mg/m$^2$ to about 200 mg/m$^2$ antibody, about 2 mg/m$^2$ to about 150 mg/m$^2$, about 5 mg/m$^2$ to about 100 mg/m$^2$, about 10 mg/m$^2$ to about 85 mg/m$^2$, about 15 mg/m$^2$ to about 75 mg/m$^2$, about 20 mg/m$^2$ to about 65 mg/m$^2$, about 25 mg/m$^2$ to about 55 mg/m$^2$, about 30 mg/m$^2$ to about 45 mg/m$^2$, or about 35 mg/m$^2$ to about 40 mg/m$^2$ antibody. In other embodiments, the therapeutically effective amount comprises about 20 mg/m$^2$ to about 90 mg/m$^2$ antibody. In one embodiment, the therapeutically effective amount comprises 30 mg/m$^2$ to about 70 mg/m$^2$ antibody. In one embodiment, the therapeutically effective amount of the nanoparticles described herein comprises about 50 mg/m$^2$ to about 200 mg/m$^2$ carrier protein or carrier protein and therapeutic agent. In a preferred embodiment, the therapeutically effective amount comprises about 75 mg/m$^2$ to about 175 mg/m$^2$ carrier protein or carrier protein and therapeutic agent. Contemplated values include any value, subrange, or range within any of the recited ranges, including endpoints.

In one embodiment, the therapeutically effective amount comprises about 20 mg/m$^2$ to about 90 mg/m$^2$ binding agent, e.g., antibody, aptamer or fusion protein. In a preferred embodiment, the therapeutically effective amount comprises 30 mg/m$^2$ to about 70 mg/m$^2$ binding agent, e.g., antibody, aptamer or fusion protein. Contemplated values include any value, subrange, or range within any of the recited ranges, including endpoints.

In one aspect, the cancer is T-cell cancer. In some embodiments, the cancer is T-cell lymphoma. In another embodiment, the cancer is peripheral T-cell lymphoma, anaplastic large cell lymphoma, angioimmunoblastic lymphoma cutaneous T-cell lymphoma, Adult T-cell Leukemia/Lymphoma (ATLL), enteropathy-type T-cell lymphoma, hematosplenic gamma-delta T-cell lymphoma, blastic NK-cell lymphoma, lymphoblastic lymphoma, nasal NK/T-cell lymphoma, treatment-related T-cell lymphoma, or the combination thereof.

In general, the compounds of this invention will be administered in a therapeutically effective amount by any of the accepted modes of administration for agents that serve similar utilities. The actual amount of the compound of this invention, i.e., the nanoparticles, will depend upon numerous factors such as the severity of the disease to be treated, the age and relative health of the subject, the potency of the compound used, the route and form of administration, and other factors well known to the skilled artisan.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) *Remington's Pharmaceutical Sciences,* 18th ed., Mack Publishing Co.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

EXAMPLES

The present disclosure is illustrated using nanoparticles composed of albumin-bound paclitaxel (i.e., ABRAX- ANE®) or cisplatin as core, and antibodies that recognize antigen(s) on or expressed by cancerous T cells (e.g., OKT3).

One skilled in the art would understand that making and using the nanoparticles of the Examples are for the sole purpose of illustration, and that the present disclosure is not limited by this illustration.

Any abbreviation used herein, has normal scientific meaning. All temperatures are ° C. unless otherwise stated. Herein, the following terms have the following meanings unless otherwise defined:

| | |
|---|---|
| ABX = | ABRAXANE ®/(albumin-bound paclitaxel |
| ACN = | acetonitrile |
| ADC = | antibody dependent chemotherapy |
| BEV = | bevacizumab |
| BSA = | bovine serum albumin |
| dH$_2$O = | distilled water |
| nM = | nanomolar |
| EdU = | 5-ethynyl-2'-deoxyuridine |
| FCB = | flow cytometry buffer |
| FITC = | Fluorescein |
| kD = | kilo-dalton |
| Kd = | dissociation constant |
| kg = | kilogram |
| KV = | kilo-volts |
| L/hr = | liter/hour |
| M = | molar |
| mCi = | millicuries |
| mg = | milligram |
| ml or mL = | milliliter |
| m$^2$ = | square meters |
| mm$^3$ = | cubic millimeter |
| OKT3 = | muromonab-CD3 |
| μg = | microgram |
| μl = | microliter |
| μm = | micrometer/micron |
| PBS = | Phosphate buffered saline |
| pK = | pharmacokinetics |
| RT = | room temperate |
| rpm = | rotations per minute |
| v = | volts |
| ×g = | times gravity |

Example 1: Nanoparticle Preparation

ABRAXANE® (ABX) is suspended in muromonab-CD3 (OKT3) with 0.9% saline. The mixture is incubated for 30 minutes at room temperature (or at the temperature indicated) to allow particle formation. For Mastersizer experiments to measure particle size of ABX:OKT3 complexes, 10 mg of ABX is suspended in OKT3 at concentrations of 0 to 25 mg/ml.

For use in humans, the ABX:OKT3 complexes may be prepared by obtaining the dose appropriate number of OKT3 and diluting each vial per the following directions to various concentrations. The dose appropriate number of 100 mg vials of ABX can be prepared by reconstituting to a final concentration containing 10 mg/mL ABX nanoparticles. Using a sterile 3 mL syringe, the OKT3 can be withdrawn and slowly injected, over a minimum of 1 minute, onto the inside wall of each of the vials containing 100 mg of ABX. The OKT3 solution should not be injected directly onto the lyophilized cake as this will result in foaming. Then, using a sterile 12 mL sterile syringe, 8.4 mL 0.9% Sodium Chloride Injection, USP, can be withdrawn and slowly injected, over a minimum of 1 minute, 8.4 mL onto the inside wall of each vial containing ABX 100 mg and OKT from 0 to 40 mg. Once the addition of OKT3 and 0.9% Sodium Chloride Injection, USP 8.4 mL is completed, each vial can be gently swirled and/or inverted slowly for at least 2 minutes until complete dissolution of any cake/powder occurs. Generation of foam should be avoided. The vials containing the ABX and OKT3 should sit for 60 minutes. The vial(s) should be gently swirled and/or inverted every 10 minutes to continue to mix the complex. After 60 minutes has elapsed, the calculated dosing volume of ABX and OKT3 should be withdrawn from each vial and slowly added to an empty viaflex bag. An equal volume of 0.9% Sodium Chloride Injection, USP is then added to the mixture of ABX and OKT3. The bag should then be gently swirled and/or inverted slowly for 1 minute to mix. The ABX:OKT3 nanoparticles can be stored for up to 4 hours at room temperature following final dilution.

Example 2: Binding of ABX and OKT3 In Vitro

To determine whether ABX and OKT3 interact, the nanoparticles formed in Example 1 are analyzed by flow cytometry and electron microscopy.

Methods

Flow Cytometry:

The nanoparticle composition comprising ABX and OKT3 is produced as described in Example 1 above. To determine binding of OKT3 to ABX, visualization of the composition is performed on an Accuri C6 flow cytometer (BD Franklin Lakes, N.J.) and data analysis is done using Accuri C6 software. Biotinylated (5 μg) goat anti-mouse IgG (Abeam, Cambridge, Mass.) is labeled with 5 μg of streptavidin PE (Abeam, Cambridge, Mass.). The goat anti-mouse IgG is chosen to label the composition because the Fab portion of the OKT3 is mouse derived. ABX and the composition are incubated with the PE-labeled goat anti-mouse IgG for 30 minutes at room temperature, washed and visualized by flow cytometry.

Electron Microscopy:

ABX, dissolved in PBS is added to a 300-mesh parlodian-carbon coated copper grid and allowed to sit for 1 minute. A pointed piece of filter paper is touched to the drop to remove excess liquid, leaving a thin film on the grid. The grids are allowed to dry. To dissolve the buffer crystals left on the dried grid, the sample is washed three times in dH$_2$0. A small drop of 1% phosphotungstic acid (PTA), pH 7.2, is added to the grid. The grid is then again touched by a pointed piece of filter paper to remove excess liquid, leaving a thin film on the grid and allowed to dry. OKT3 in 0.9% sodium chloride solution is diluted with PBS at 1:10 ratio. OKT3 is loaded on nickel formvar-coated grid and allowed to air dry for 30 minutes to 1 hour. For the composition, ABX dissolved in PBS, and OKT3 in 0.9% sodium chloride solution, are mixed. The complex is further diluted with PBS at 1:5. The complex is loaded on nickel formvar-coated grid and air dried for 30 minutes to 1 hour. Both samples are incubated for 1 hour in goat anti-mouse IgG with 6 nm gold-conjugated particles (Electron Microscopy Sciences), diluted 1:30 with 10% FCB/PBS, washed 6 times with PBS (each 2 minutes), 6 times with dH$_2$O, then stained with the mixture of 2% methylcellulose and 4% UA (9:1) for 5 minutes. Filter paper is used to drain the stain and the grid is air dried for 1 hour. Both samples are incubated overnight in donkey anti-mouse IgG with 6 nm gold-conjugated particles (Jackson ImmunoResearch) diluted 1:25 with 10% FCB/PBS, washed 6 times with PBS (each 2 minutes), 6 times with dH$_2$0 water, stained with 1% PTA for 5 minutes, air dried, covered with 2% methylcellulose, and air dried for 1 hour. The micrographs are taken on a JEOL1400 at operating at 80 KV.

Example 3: Function of the Nanoparticle Composition In Vitro

The experiment is to confirm that the two key elements in the complexes, the antibody and the paclitaxel, retain their functions when present in the complexes.

In Vitro Toxicity:

The HuT-78 human T-cell lymphoma cell line (ATCC Manassas, Va.) are cultured in RPMI 1640 medium supplemented with 4.5 g/L glucose, L-glutamine, and 10% fetal bovine serum (MG-72, CLS order number 820702). Cells are harvested and plated at $10^6$ cells per well in 24 well plates. Cells are exposed to ABX or the composition at paclitaxel concentrations from 0 to 200 µg/ml overnight at 37° C. and 5% $CO_2$. To measure proliferation, the Click-iT EdU (Molecular Probes, Eugene, Oreg.) kit is utilized. Briefly, 10 mM EdU is added to the wells and incubated overnight with the cells and ABX or the nanoparticle composition. The cells are permeabilized with 1% saponin and intercalated EdU is labeled with a FITC-conjugated antibody. The proliferation index is determined by dividing the FITC positive cells from each treatment by the maximum proliferation of untreated EdU labeled cells.

VEGF ELISA:

To determine whether OKT3 can still bind its ligand, CD3, when bound to ABX, a standard CD3 ELISA is used. The composition is prepared as described and CD3-Ig fusion proteins are added to the composition with complex or ABX alone. The CD3-Ig fusion protein is incubated with the nanoparticles for 2 hours at room temperature. The suspension is spun at 6000 rpm for 15 minutes, supernatants are collected and free fusion protein is measured by ELISA. Absorbance is measured by a Versamax ELISA plate reader (Molecular Devices, Sunnyvale, Calif.). The concentration of unbound VEGF is determined with a standard curve from 0 to 2000 pg/ml.

Example 4: Particle Size

To understand the characteristics of the nanoparticles formed when binding OKT3 to ABX, the size of the ABX: OKT3 complexes is determined relative to ABX.

Mastersizer and Nanosight:

The particle size of ABX and antibody-ABX drug complexes are measured by dynamic light scattering on a Mastersizer 2000 (Malvern Instruments, Westborough, Mass.). To measure particle size, 2 ml (5 mg/ml) of ABRAXANE® or complex is added to the sample chamber. Data are analyzed with Malvern software and particle size distributions are displayed by volume. The particle sizes and stability are later validated using the Nanosight System (Malvern Instruments, Westborough, Mass.). The ABX or complex particles are diluted to the appropriate range to accurately measure particle sizes. Data is displayed by particle size distribution; however, the nanoparticle tracking analysis uses Brownian motion to determine particle size.

Example 5: Protein Affinity

To understand the characteristics of the nanoparticles formed when binding OKT3 to Abraxane, the binding affinity of the complex was determined by a Bio-layer interferometry (BLItz) assay, which is an optical technology that uses interference of white light reflection to determine binding affinities of 2 proteins In a BLItz assay, if the 2 proteins bind, the reflected light changes wavelength in a manner that correlates to the binding affinity of the 2 proteins. Here biotinylated OKT3 at 100 ug/ml was immobilized on a streptavidin-containing probe and exposed to Abraxane at 2 concentrations-500 ug/ml (Run 2) and 1000 ug/ml (Run 3)

In the case of the anti-human CD3 antibody (OKT3) and Abraxane, biotinylated OKT3 at 100 ug/ml was immobilized on a streptavidin-containing probe. The OKT3 bearing probe was then immersed in Abraxane at 2 concentrations, 500 ug/ml and 1000 ug/ml (Run 2 and Run 3). Then Abraxane was bound to OKT3 in a concentration dependent manner. The association and dissociation constants on the proteins were calculated by the BLItz software. See FIG. 18.

The results show the dissociation constant of OKT3 and Abraxane was $2.246 \times 10^9$, which suggests a strong non-covalent bond between these two proteins.

Example 6: Efficacy of the ABX:OKT3 Complex in Mice

A xenograft model of HuT-78 human T-cell lymphoma cells implanted into athymic nude mice is employed to test the efficacy of the composition with ABX:OKT3 complex in vivo.

In vivo experiments are performed at least 2 times. The number of mice required for those experiments is determined by power analysis. Mouse tumors are measured 2-3 times/week and mice are sacrificed when the tumor is 10% by weight. Mice that has complete tumor responses are monitored for 60-80 days post-treatment. The end point of the mouse studies is median survival. Kaplan-Meier curves are generated and Mantle-Cox test is performed to determine significance of median survival between treatment groups. The in vitro results presented are representative of at least 5 repeated experiments. Statistical analyses of in vitro and in vivo percent change from baseline experiments are done using the Student's t-test.

Mouse Model:

To test tumor efficacy, $1 \times 10^6$ HuT-78 human T-cell lymphoma cells are implanted into the right flank of athymic nude mice (Harlan Sprague Dawley, Indianapolis, Ind.). When the tumors reach a size of about 700 $mm^3$, the mice are randomized and treated with PBS, ABX, OKT3 (12 mg/kg), OKT3 followed by ABX, or the composition as described above at the above concentrations. For the mouse experiments testing bigger nanoparticles, the highest dose of OKT3 necessary to create the larger particles is used in the OKT3-only treatment group. Tumor size is monitored 3 times/week and tumor volume is calculated with the following equation: (length×width$^2$)/2. Mice are sacrificed when the tumor size equaled 10% of the mouse body weight or about 2500 $mm^3$. The day 7 percent change from baseline is calculated as follows: [(tumor size on treatment day-tumor size on day 7)/tumor size on treatment day]×100.

Example 7: Paclitaxel Pharmacokinetics in Mice

To compare the pharmacokinetics (pk) of the composition and ABX, plasma paclitaxel concentrations are measured in mice administered composition or ABX at 0, 4, 8, 12 and 24 hours.

Methods

Paclitaxel Pharmacokinetics:

The liquid chromatographic separation of paclitaxel and d5 paclitaxel are accomplished using an Agilent Poroshell 120 EC-C18 precolumn (2.1×5 mm, 2.7 µm, Chrom Tech, Apple Valley, Minn.) attached to an Agilent Poroshell 120 EC-C18 analytical column (2.1×100 mm, 2.7 µm Chrom Tech, Apple Valley, Minn.) at 40° C., eluted with a gradient mobile phase composed of water with 0.1% formic acid (A) and ACN with 0.1% formic acid (B) with a constant flow rate of 0.5 ml/minute. The elution is initiated at 60% A and 40% B for 0.5 minutes, then B is linearly increased from 40-85% for 4.5 minutes, held at 85% B for 0.2 minutes, and returned to initial conditions for 1.3 minutes. Autosampler temperature is 10° C. and sample injection volume is 2 µl. Detection of paclitaxel and the internal standard d5-paclitaxel are accomplished using the mass spectrometer in positive ESI mode with capillary voltage 1.75 kV, source temp 150° C., desolvation temp 500° C., cone gas flow 150 L/hr, desolvation gas flow 1000 L/hr, using multiple reaction monitoring (MRM) scan mode with a dwell time of 0.075 seconds. The cone voltages and collision energies are determined by MassLynx-Intellistart, v4.1, software and varied between 6-16 V and 12-60 eV, respectively. The MRM precursor and product ions are monitored at m/z 854.3>105.2 for paclitaxel and 859.3>291.2 for d5 paclitaxel. The primary stock solutions of paclitaxel (1 mg/ml in EtOH) and d5 paclitaxel (1 mg/ml in EtOH) are prepared in 4 ml amber silanized glass vials and stored at −20° C. Working standards are prepared by dilution of the stock solution with ACN in 2 ml amber silanized glass vials and stored at −20° C. Plasma samples are extracted as follows, 100 µl plasma sample is added to a 1.7 ml microcentrifuge tube containing d5 paclitaxel (116.4 nM or 100 ng/ml) and 300 µl ACN, vortexed, incubated at room temperature for 10 minutes to precipitate proteins, and centrifuged (14,000 rpm) or 3 minutes. The supernatant is filtered on an Agilent Captiva ND$^{lipids}$ plate (Chrom Tech, Apple Valley, Minn.), collected in a deep 96-well plate, and dried using nitrogen gas. The samples are reconstituted using 100 µl ACN and shaken on a plate shaker (high speed) for 5 minutes. Plasma standard curves are prepared daily containing paclitaxel (0.59-5855 nM or 0.5-5000 ng/ml) and d5 paclitaxel (116.4 nM) for paclitaxel quantitation. Mouse tumors are thawed on ice, weighed, and diluted 2 parts (weight to volume) in 1×PBS. Tumors are then homogenized using a PRO200 tissue homogenizer using the saw tooth probe (5 mm×75 mm). Tumor homogenate is than processed the same as the human plasma samples.

Mouse Imaging:

Briefly, Tris Buffer (0.125 M Tris-HCl, pH 6.8, 0.15 M NaCl) and 5 mCi Na$^{125}$ are added directly to iodination tubes (ThermoFischer Scientific, Waltham, Mass.). The iodide is allowed to activate and is swirled at room temperature. Activated iodide is mixed with the protein solution. 50 µl of Scavenging Buffer (10 mg tyrosine/mL in PBS, pH 7.4) is added and incubated for five minutes. After addition of Tris/BSA buffer and mixing, samples are applied in 10K MWCO dialysis cassettes against pre-cooled PBS for 30 minutes, 1 hour, 2 hours, and overnight at 4° C. Radioactivity is determined by Gamma counter, then disintegrations per minute (DPM) and specific activity are calculated. Mice are injected in their tail vein with OKT3, ABX-OKT3, ABX-human IgG, human IgG, and ABX only. Animals are imaged at 3, 10, 24 and 72 hours post-administration via SPECT-CT imaging using the U-SPECT-II/CT scanner (Ml-Labs, Utrecht, The Netherlands). SPECT reconstruction is performed using a POSEM (pixelated ordered subsets by expectation maximization) algorithm. CT data are reconstructed during the Feldkamp algorithm. Co-registered images are further rendered and visualized using PMOD software (PMOD Technologies, Zurich, Switzerland). Animals are sacrificed and dissected at 72 hours post-injection. Selected tissues and organs of interest are measured using radioisotope dose calibrator (Capintec CRC-127R, Capintec Inc.).

Example 8: Lyophilization of the Nanoparticle Composition

The nanoparticle composition is synthesized by adding OKT3 to ABRAXANE®. 0.9% saline is then added for a final volume of 2 ml, and the mixture is allowed to incubate at room temperature for 30 minutes in a 15 ml polypropylene conical tube.

After the 30 minute room temperature incubation, the mixture is diluted 1:2 in 0.9% saline, respectively. These are the concentrations of the 2 drugs when prepared by the pharmacy for administration to patients.

The nanoparticle composition is divided into twenty 200 µl aliquots in 1.5 ml polypropylene eppendorfs and frozen at −80° C.

Once frozen, the aliquots are lyophilized overnight with the Virtis 3L benchtop lyophilizer (SP Scientific, Warmister, Pa.) with the refrigeration on. A lyophilized preparation is generated.

The dried aliquots are stored at room temperature in the same 1.5 ml polypropylene eppendorfs. These samples are readily reconstituted in saline at room temperature for 30 minutes, followed by centrifugation for 7 minutes at 2000× g. The resulting sample is then resuspended in the appropriate buffer, as needed.

By comparison, a sample that is dried with heat and a speed vacuum is impossible to reconstitute.

Example 9: Testing of Lyophilized Preparations

Samples are reconstituted at different time points after lyophilization and tested for their physical properties against ABX, and freshly made nanoparticle composition.

Particle size distribution is evaluated as described above.

CD3 binding is evaluated by incubation of the sample with CD3-IgG fusion proteins for 2 hours at room temperature, centrifuged at 2000×g for 7 minutes. The amount of CD3 bound to the pellet (corresponding to the nanoparticles) or remaining in the supernatant is measured with ELISA.

Paclitaxel activity is assessed by cytotoxicity against HuT-78 human T-cell lymphoma cells in vitro.

Example 10: Follow Up Study to Investigate Whether Pretreatment with OKT3 Improves Targeting Following the general protocol above, athymic nude mice are injected with 1×10$^6$ HuT-78 cells in the right flank and then treated with PBS, OKT3, ABX, the nanoparticle composition, or pretreated with OKT3 and, 24 hr later, the nanoparticle composition. Data is represented at day 7-post and day 10-post treatment as tumor volume in mm$^3$. The tumor sizes are tracked over 10 days.

What is claimed is:

1. A nanoparticle composition comprising nanoparticles having an outer surface, wherein each of the nanoparticles comprises:
   (a) a carrier protein,
   (b) a binding agent with a T-cell antigen-binding portion, and
   (c) a therapeutically effective amount of paclitaxel;
   wherein upon reconstitution with an aqueous solution, the antigen-binding portion of said binding agents are capable of binding to a T-cell antigen in vivo.

2. The nanoparticle composition of claim 1, wherein the nanoparticle comprises about 100 to about 1000 binding agents.

3. The nanoparticle composition of claim 1, wherein the antigen-binding portion is capable of binding to a T-cell receptor.

4. The nanoparticle composition of claim 3, wherein the antigen-binding portion binds to an antigen selected from CD2, CD3, CD4, CD5, CD8, CD25, CD30, CD40, CD52, CD 122, or CCR4.

5. Then nanoparticle composition of claim 1, wherein the nanoparticle is lyophilized.

6. The nanoparticle composition of claim 1, wherein the composition is stable at about 20° C. to about 25° C. for up to about 12 months or longer.

7. The nanoparticle composition of claim 1, wherein the binding agent comprises Slipizumab, muromonab-CD3 (OKT3), Leu 1, Zanolimumab, Brentuximab vedotin, Mik-β1, KW-0761, or a combination thereof.

8. The nanoparticle composition of claim 1, wherein the binding agent is muromonab-CD3 (OKT3).

9. The nanoparticle composition of claim 1, wherein the antigen binding portion comprises an aptamer, a receptor ligand, an Fab fragment, or a combination thereof.

10. The nanoparticle composition of claim 1, wherein the composition comprises one or more additional cancer therapeutic agents.

11. The nanoparticle composition of claim 10, wherein the additional cancer therapeutic agent comprises abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, or cyclophosphamide.

12. The nanoparticle composition of claim 1, wherein fewer than about 50% of said nanoparticles are oligomeric.

13. The nanoparticle composition of claim 1, wherein the average size of the nanoparticles is between 90 nm and 800 nm.

14. The nanoparticle composition of claim 1, wherein the carrier protein comprises albumin, gelatin, elastin, gliadin, legumin, zein, a soy protein, a milk protein, a whey protein, or a combination thereof.

15. The nanoparticle composition of claim 14, wherein the carrier protein comprises an antibody-binding motif.

16. The nanoparticle composition of claim 15, wherein the carrier protein is albumin.

17. The nanoparticle composition of claim 16, wherein the albumin is human serum albumin.

18. The nanoparticle composition of claim 16, wherein the albumin is recombinant human serum albumin.

19. The nanoparticle composition of claim 1, wherein the composition is formulated for intravenous delivery.

* * * * *